United States Patent [19]
Yoshida et al.

[11] Patent Number: 5,843,713
[45] Date of Patent: Dec. 1, 1998

[54] PEPTIDE SEQUENCE THAT FORMS MUCIN SUGAR CHAIN AND TECHNIQUE FOR MODIFYING PROTEIN TO BE LINKED WITH MUCIN SUGAR CHAIN

[75] Inventors: Aruto Yoshida; Makoto Takeuchi, both of Yokohama, Japan

[73] Assignee: Kirin Beer Kabushiki Kaisha, Tokyo, Japan

[21] Appl. No.: 666,473

[22] PCT Filed: Nov. 1, 1995

[86] PCT No.: PCT/JP95/02238

§ 371 Date: Sep. 19, 1996

§ 102(e) Date: Sep. 19, 1996

[87] PCT Pub. No.: WO96/13516

PCT Pub. Date: May 9, 1996

[30] Foreign Application Priority Data

Nov. 1, 1994 [JP] Japan .................................. 6-269111
Feb. 9, 1995 [JP] Japan .................................. 7-022101

[51] Int. Cl.$^6$ .......................... C12P 21/06; C12P 21/04; C12N 5/00; C07H 21/02
[52] U.S. Cl. ................... 435/69.1; 435/70.1; 435/172.1; 435/320.1; 435/325; 536/23.1; 536/23.4; 935/22
[58] Field of Search .................... 435/69.1, 70.1, 435/172.1, 193, 325, 320.1, 97; 536/23.1, 23.4; 935/22

[56] References Cited

PUBLICATIONS

Wilson et al (1991) BiocJ 275:529–534 "Amino acid distributions aroud O–linked glycosylation sites".
Brockhausen et al (1990) Biochem 29:10206–10212 "Control of Mucin synthesis: The peptide portion of . . . ".
Grabenhorst et al (1993) Eur J. Biochem 275:189–197 "Biosynthesis and secretion of human interleukin 2 glycoprotein . . . ".

Primary Examiner—Rebecca E. Prouty
Assistant Examiner—Einar Stole
Attorney, Agent, or Firm—Foley & Lardner

[57] ABSTRACT

An amino acid sequence that can specifically introduce a mucin type sugar chain into a protein or peptide chain and a technique of introducing a mucin type sugar chain into protein or peptide by utilizing such a sequence are disclosed. GalNAc moiety of UDP-GalNAc (where UDP represents uridine 5'-diphosphate and GalNAc represents N-acetylgalactosamine) is introduced into the amino acid X(O) in the presence of UDP-GalNAc: polypeptide α1, O-GalNAc transferase (O-GalNAc T):

$$X(-1)\text{-}X(0)\text{-}X(1)\text{-}X(2)\text{-}X(3) \tag{I}$$

where X(-1) and X(2) represent independently any amino acid, X(O) represents T or S and X(1) and X(3) represent independently any amino acid except that at least one of X(1) and X(3) represents P.

13 Claims, 23 Drawing Sheets

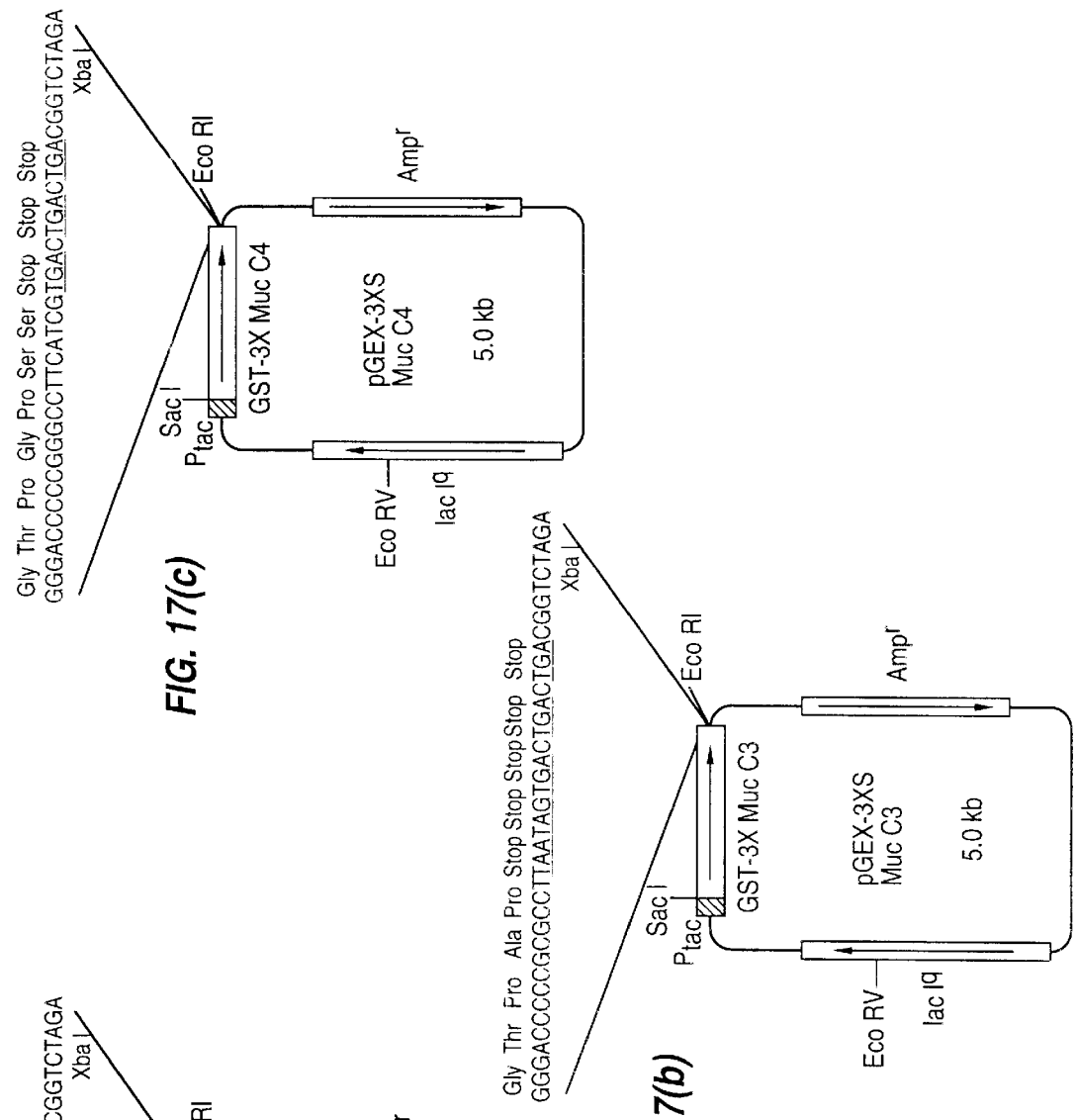
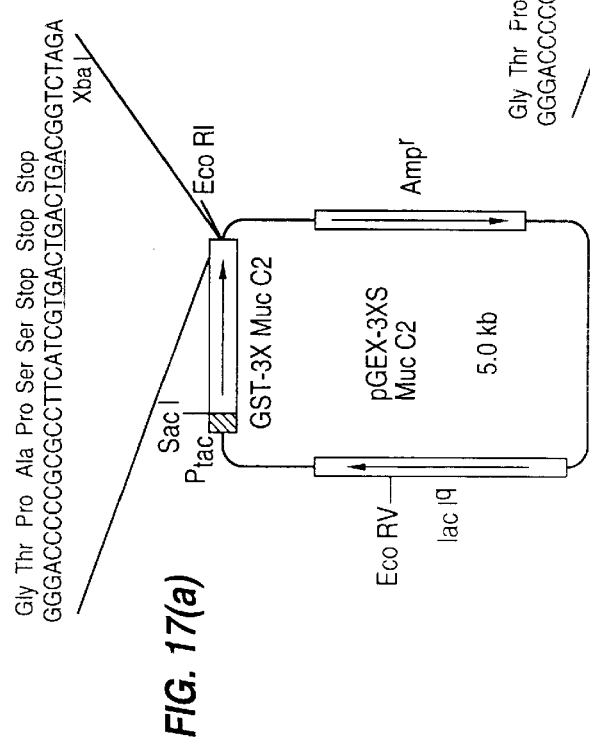
FIG. 17(a)
FIG. 17(b)
FIG. 17(c)

| | | |
|---|---|---|
| 1 | EGST-3X | UNTREATED |
| 2 | EGST-3X | INCUBATED AT 37°C |
| 3 | EGST-3X | TREATED WITH NEURAMINIDASE |
| 4 | EGST-3X | TREATED WITH NEURAMINIDASE AND O-GLYCANASE |
| 5 | EGST-3X Muc C1 | UNTREATED |
| 6 | EGST-3X Muc C1 | INCUBATED AT 37°C |
| 7 | EGST-3X Muc C1 | TREATED WITH NEURAMINIDASE |
| 8 | EGST-3X Muc C1 | TREATED WITH NEURAMINIDASE AND O-GLYCANASE |

PEPTIDE SEQUENCE THAT FORMS MUCIN SUGAR CHAIN AND TECHNIQUE FOR MODIFYING PROTEIN TO BE LINKED WITH MUCIN SUGAR CHAIN

BACKGROUND OF THE INVENTION

1. Field of the Invention

This invention relates to amino acid sequences with which a mucin type sugar chain can be introduced into a protein or peptide and also relates to a technique for introducing a mucin type sugar chain into a protein or peptide by utilizing the sequences.

2. Background Art

Many of the proteins found in animals, plants and insects are glycoproteins. A wide variety of roles of the sugar chains of glycoprotein has been unveiled in recent years. For example, it is known that a sugar chain has physiological roles as a ligand in cell adhesion and cell recognition as well as a physicochemical role of improving the stability and/or solubility of proteins. In addition, while glycoproteins such as erythropoietin and interferons have been developed as a drug recent years, the structure of the sugar chain on the glycoproteins has a great influence on the pharmacokinetics and the stability of the drugs in vivo. Although the significance of the sugar chains of glycoprotein has been well recognized, no established techniques have been known so far for introducing a sugar chain into a specific position of a protein in a simple manner.

For some drugs that are inherently glycoprotein, their protein portions are only prepared typically with *E. coli* on a mass production basis. When such a protein is administered as a drug, the kinetics, stability and antigenicity of the protein in vivo sometimes differ from the native glycoprotein due to lack of sugar chains. The differences may, by turn, give rise to problems including impairment with a large dose and side effect.

Even proteins produced in animal cells can become glycoproteins having sugar chains that are different from the native ones. Then, such proteins can also entail the problems as mentioned above.

The above problems and other related problems may be dissolved by a technique of introducing a specific sugar chain into a specific position of a protein molecule. Further, various functional features of sugar chains can be selectively introduced into the protein with such a technique. Furthermore, the technique will show a wide variety of applications in the pharmaceutical industry and other industries.

Two major modes of binding a sugar chain to protein have been known; an asparagine linked type sugar chain and a mucin type sugar chain.

According to previous reports, asparagine linked type sugar chains attach to a consensus sequence of -Asn-Xaa-Ser/Thr- (Xaa≠Pro). However, it is also known that not all the sites having the consensus sequence in a protein have an asparagine linked type sugar chain. On the other hand, as for the mucin type sugar chain, there have been reports telling that amino acids such as Ser, Thr and Pro are frequently observed near the binding site. However, no reports have ever described the well characteristic features of the sequence of the binding site.

The asparagine linked type sugar chain differs from the mucin type sugar chain in the biosynthesis of the sugar chain. Specifically, the biosynthesis of an asparagine linked type sugar chain takes place co-translationally in protein synthesis and then the folding of glycoprotein follows it. On the other hand, a mucin type sugar chain is introduced post-translationally, i.e., after the translation and folding of protein. In addition, as for the asparagine linked type sugar chain, it has been reported that a large sugar chain having fourteen monosaccharides is at a time transferred to a protein and recognized and controlled to form a proper protein structure by a molecular chaperon called calnexin. However, no molecular chaperon is known to date for the mucin type sugar chains.

Thus, while common sequence required for glycosylation of an asparagine linked type sugar chain is well known as described above, there is no knowing where is the suitable position in a protein for introducing the sugar chain. In addition, there is no guarantee if the mutant protein having the sugar chain shows the same three dimensional structure and biological activity as its native protein.

For the mucin type sugar chain, on the other hand, it may be safely assumed that the structure of a protein molecule is not significantly affected by introduction of a sugar chain, because the sugar chain is introduced after the protein folding. Therefore, the technique for introducing the mucin type sugar chain into a protein may be very promising for providing protein having functional features of sugar chains, while maintaining the protein structure and activities unchanged. However, no structural features which are highly specific to the glycosylation site for a mucin type sugar chain have been found. Therefore, it is impossible to specifically introduce a mucin type sugar chain into a certain portion of a protein molecule to date.

While some characteristic aspects of peptide sequences around mucin type sugar chain binding sites are known as will be described hereinafter, an enzyme to introduce GalNAc (N-acetylgalactosamine) of a mucin type sugar chain into proteins is also known. This enzyme is called UDP-GalNAc: polypeptide α1, O-GalNAc transferase (O-GalNAc T). Further, O-GalNAc T is found in colostrum of cow and catalyzes a reaction in which GalNAc is transferred into serine or threonine of a protein or peptide as follows:

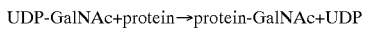

wherein UDP represents uridine 5'-diphosphate and GalNAc represents N-acetylgalactosamine.

The enzyme is found in a variety of sources. For instance, it was found in colostrum of cow by A. Elhammer et al. [J. Biol. Chem., Vol.261, pp.5249–5255, (1986)], in rat ascites hepatoma cells, AH99 by M. Sugiura et al. [J. Biol. Chem., Vol.257, pp.9,501–9,507 (1982)], in porcine submaxillary gland by Y. Wang et al. [J. Biol. Chem., Vol.267, pp.12709–12716(1992)], in pig trachea by J. M. Cottrell et al. [Biochem. J., Vol.283, pp.299–305 (1992)]. Further, the success in cloning the genes of the enzyme has been reported [F. L. Homa et al., J. Biol. Chem., Vol.268, pp.12609–12616 (1993)]. It has been also reported that a large amount of the enzyme can be obtained in insect cells and animal cells by means of genetic engineering techniques [F. L. Homa et al., Protein Expr. Purif., Vol.6, pp.141–148 (1995) and S. Wragg et al., J. Biol. Chem., Vol.270, pp.16947–16954 (1995)].

Although several studies on characteristic aspects of peptide sequences binding mucin type sugar chains have been reported, they mostly rely on statistic methods with which amino acid sequences are analyzed particularly at and around the sites where mucin type sugar chains are bound. Very few of them deal with the actual use of the peptide thus obtained with O-GalNAc T in order to analyze the reactivity of the peptide sequences.

I. B. H. Wilson et al. compared peptide sequences of glycosylation sites of mucin type sugar chains with those of non-glycosylation sites. Thus, they reported that proline, serine and threonine are frequently found at positions between −3 and +3 of each binding site. (hereinafter, with regard to the locations of amino acids in a peptide sequence, the position to which a sugar chain is transferred is denoted as Position 0 and positions next to Position 0 and sequentially approaching the N-terminal are respectively referred to as Positions −1, −2 and −3 in order, whereas positions next to Position 0 and sequentially approaching the C-terminal are respectively referred to as Positions +1, +2 and +3 in order.) Further, proline is found at Positions −1 and +3 with a relatively high frequency. However, they concluded that it is difficult to definitely describe the characteristic features of the sites suitable for binding mucin type sugar chains, because the specific sequences they found are also found at positions other than the binding site. Furthermore, they did not carry out actual experiments on peptide in order to confirm their statistic findings, either [Biochme. J., Vol. 275, pp.529–534(1991)].

A. A Gooley et al. analyzed the sugar chain binding site of a mucin type glycoprotein of rat called CD8 α with Edman degradation. Thus, they proposed a motif of Xaa-Pro-Xaa-Xaa (where at least one of the Xaa's represents threonine binding a mucin type sugar chain) that can be used as a consensus sequence for glycosylation site of a mucin type sugar chain. However, the motif is not feasible for a wide scope of application since it cannot satisfactorily define the mucin type sugar chain binding site of glycoproteins derived from other sources [Biochem. Biophys. Res. Commun., Vol.178, pp.1194–1201 (1991)]. Later, they also analyzed human glycophorin A [Glycobiology, Vol.4, pp.413–417 (1994)] and bovine κ-casein [Glycobiology, Vol.4, pp.837–844 (1994)], which are also mucin type glycoproteins, in a similar manner. As a results, they proposed the following four motifs as an extension of the preceding proposal. In the following, Thr(GalNAc) represents a threonine residue binding a mucin type sugar chain.

1. Xaa-Pro-Xaa-Xaa where at least one of the Xaa's represents Thr(GalNAc),
2. Thr(GalNAc)-Xaa-Xaa-Xaa where at least one of the Xaa's represents threonine,
3. Xaa-Xaa-Thr(GalNAc)-Xaa where at least one of the Xaa's represents lysine or arginine, and
4. Ser(GalNAc)-Xaa-Xaa-Xaa where at least one of the Xaa's represents serine.

With this extension, however, the motifs do not satisfactorily define the sugar chain introducing site of glycoproteins of other mucin types. Furthermore, the above motifs may cover peptide sequences having no sugar chain and hence some limitations have to be defined for Xaa's. In addition, they have not verified the motifs by actually applying them to peptide.

J. D. Young et al. reported that the activity of a GalNAc acceptor can be measured in vitro by utilizing O-GalNAc T derived from swine submaxillary gland and a synthesized peptide as a substrate (Biochemistry, Vol.18, pp.4444–4448 (1979)]. Their report says that TPPP, RTPPP, PRTPPP, TPRTPPP and VTRTPPP (SEQ ID NOS:10, 6, 108, 109 and 7, respectively) which are derived from bovine myelin basic protein are highly active GalNAc acceptors and VTRTPPP (SEQ ID NO:7) is the most active among them. However, the sequences may not be feasible as characteristic features in GalNAc acceptor because of a small number of studied analogous peptides. In addition, the fact that proline is found at all Positions +1 to +3 can significantly limit the applicability of these peptides for introducing mucin type sugar chains into protein or peptide.

B. O'Connell et al. carried out a statistic analysis on sites for binding mucin type sugar chains and predicted that the amino acids at Positions −6, −1 and +3 are important. They actually synthesized peptides by modifying a peptide having twelve amino acid residues, PHMAQVTVGPGL (SEQ ID NO:114) (Positions −6 through +5), which is found at and near the site binding a sugar chain of human von Willebrand factor, by changing the amino acids at Positions −6, −1 and +3 for other three different amino acids (arginine, glutamic acid, proline or isoleucine) in order to confirm their influence on GalNAc acceptor activity. However, they failed to discover characteristic features of peptide sequence necessary for binding mucin type sugar chains and simply concluded that amino acid substitution at any position can significantly affect the GalNAc acceptor activity [Biochim. Biophys. Res. Commun., Vol.180, pp.1024–1030 (1991)].

Later, B. O'Connell et al. prepared peptides by substituting the amino acids at Positions −6 through +5 of the same peptide with five amino acids (arginine, glutamic acid, proline, isoleucine and alanine) and studied their influence on the GalNAc acceptor activity. As a result, they have reported that the activity is adversely affected when the amino acids at Positions +3, −3 and −2 are substituted by different amino acids or the amino acid at Position −1 is substituted by an electrically charged amino acid, while the remaining positions have little influence on the GalNAc acceptor activity. These results are inconsistent with their previous report above. This indicates that the statistic analysis has little to do with the actual binding reactivity of mucin type sugar chain. They studied the position at which any amino acid substitution decreased the activity. Therefore, they failed to show what amino acids can favorably be used for such substitution in general because they used only limited amino acids. Thus, they could not draw general conclusions on peptide sequences binding mucin type sugar chains [J. Biol. Chem., Vol.267, pp.25010–25018 (1992)].

Ake P. Elhammer et al. statistically analyzed Positions −4 through +4 of peptides and prepared an algorithm to support a theory that the peptide sequence is not important in terms of sites for binding mucin type sugar chains so long as the binding site and its neighborhood comprise serine, threonine, proline, alanine and/or glycine. Further, they proposed PPASTSAPG as a possible ideal peptide sequence for introducing a mucin type sugar chain. The proposed peptide actually had the highest degree of GalNAc acceptor activity when compared with other four peptide sequences including RTPPP. However, since the comparison was limited only to four types of peptide sequences containing similar sequences, there remains a doubt that the proposed sequence is really ideal. In addition, it was shown that GalNAc can not be introduced into a protein having a large number of sites which are to be a binding site according to their algorithm. Therefore, the proposed sequence will not feasibly be used for introducing mucin type sugar chains into a variety of protein [J. Biol. Chem., Vol.268, pp.10029–10038 (1993)].

Glycoprotein "mucin", after which the word of mucin type sugar chain named, comprises a region where amino acid sequences having 20 to 30 residues are repeated in tandem. It is also known that a large number of mucin type sugar chains are bound in that region. I. Nishimori et al. prepared various peptides analogous to the repetitive region of human mucin MUC1 and studied the GalNAcT acceptor activity by using a crude enzyme solution of O-GalNAc T extracted from human breast cancer cells MCF7 [J. Biol.

Chem., Vol.269, pp.16123–16130 (1994)]. They reported that, as a result of their study, the peptide region essentially required for the GalNAc acceptor covers Positions −1 through +4 and, further, the proline at Position +3 can accelerate the transfer of GalNAc. On the other hand, they emphasized that the proline at Position +3 alone cannot provide any sufficient GalNAc acceptor activity because no transfer of GalNAc is observed on PDTRPAPGS (SEQ ID NOS :110–112), PDTRPPAGS and PDTRAPPGS. Although they presumed that aspartic acid and arginine at Positions −1 and +1 provide major factors that obstruct the transfer, they did not carry out any experiment to confirm their theory. Therefore, it is difficult to fully realize the characteristic features of peptide sequence that provide the GalNAc acceptor activity from their conclusions.

As examples of preparation of mucin type glycoprotein by introducing sequences for binding mucin type sugar chain into protein with genetic engineering, E. Gravenhorst et al. reported that they introduced mucin type sugar chains into interleukin 2 (IL-2) [Eur. J. Biochem, Vol.215, pp.189–197 (1993)]. They initially tried to introduce GGKAPTSSST-KGG (SEQ ID NO:29), which included a sequence found on the periphery of the site binding a mucin type sugar chain in IL-2, between the 80th and the 81st amino acids of IL-2 and express the sequence in an insect cell but they failed. Thereafter, they succeeded in introducing a sugar chain by using GGKAPTPPPKGG (SEQ ID NO:113) where all the serine residues of the above sequence were changed with proline residues. However, the sequence may have been obtained by mere chance as a result of trial and error process. Furthermore, the peptide sequence may not find a wide applicability in view of the fact that the peptide sequence was long and contained as many as twelve residues, of which four were proline residues capable of greatly influencing the configuration of protein.

As described above, the characteristic features of peptide sequence for binding mucin type sugar chains can greatly vary depending on the selected population and the techniques used for statistic processings where statistic analysis is involved. This is probably because it is technically very difficult to definitely know the sites biding mucin type sugar chains in natural proteins and hence quite a limited number of sites for binding sugar chains have been identified so far. In many cases, the characteristic features obtained for certain peptide sequences can differ from sequences found in native proteins having GalNAc acceptor activity and, therefore, may not be accurate.

On the other hand, a small number of reports on the GalNAc acceptor activity of synthesized peptide are known. The number of peptides that have been analyzed so far is limited simply because peptide synthesis per se is difficult. Most of the peptide sequences that have been studied are relatively long ones having ten or more residues and the characteristic features of short peptide sequences that can suitably be used for introducing mucin type sugar chains are to be unveiled.

Thus, it is very difficult to intentionally introduce a mucin type sugar chain into protein on the basis of the previously described characteristic features of peptide sequence that have been reported. Furthermore, since peptide sequences that are believed to be suitable for introducing mucin type sugar chains are relatively long, a mucin type sugar chain cannot be introduced simply by slightly modifying a protein or peptide. Therefore, the scope of utilization of the peptide sequences has been very limited.

In the meantime, it might be possible to chemically synthesize a protein binding sugar chains. However, as may be understood by looking at natural mucin glycoproteins, sugar chains have to be bound only to specific residues among a large number of serine or threonine residues in protein. It is thus extremely difficult to selectively and efficiently introduce a sugar chain into a specific site among a large number of serine and threonine residues in a protein or peptide by means of any known techniques for organic synthesis.

SUMMARY OF THE INVENTION

As a result of research efforts on peptide sequences as a site suitable for binding mucin type sugar chains, we have now found short peptide sequences into which mucin type sugar chains can be introduced efficiently. The present invention is based on this finding.

Therefore, an object of the present invention is to provide peptide sequences as a binding site into which mucin type sugar chains can be introduced.

Another object of the present invention is to provide peptide sequences into which mucin type sugar chains can be introduced by means of a catalytic activity of O-GalNAc T.

Still another object of the present invention is to provide a technique capable of introducing mucin type sugar chains into a protein by minimum mutation of the protein without damaging its functional features.

A protein or peptide according to the invention comprises a sequence represented by the following formula (I):

wherein
X(-1) and X(2) represent independently any amino acid,
X(0) represents threonine (T) or serine (S),
X(1) and (3) represent independently any amino acid provided that at least one of X(1) and X(3) represents proline (P).

The protein or peptide represented by the above formula can function as a substrate for UDP-GalNAc: polypeptide α1,O-GalNAc transferase (O-GalNAc T) and can be used for introducing GalNAc into a protein or peptide.

According to the present invention, there is also provided a method of introducing GalNAc into a protein or peptide, comprising the steps of providing a protein or peptide including a sequence represented by formula (I), and reacting the protein or peptide as a substrate with UDP-GalNAc (where UDP represents uridine 5'-diphosphate and GalNAc represents N-acetylgalactosamine) in the presence of UDP-GalNAc: polypeptide α1,O-GalNAc transferase ( O-GalNAc T).

According to the present invention, there is also provided a method of preparing a glycoprotein having mucin type sugar chains, comprising the steps of providing a DNA coding for a protein or peptide containing a sequence represented by formula (I) and secretory expressing the DNA in eucaryotic cells.

BRIEF DESCRIPTION OF THE DRAWINGS

FIGS. 17A, 17B and 17C are charts showing the structures of plasmids pGEX-3XS Muc C2, pGEX-3XS Muc C3 and pGEX-3XS Muc C4 for the expression of proteins GST-3X Muc C2, GST-3X Muc C3 and GST-3X Muc C4, respectively (SEQ ID NOS:121, 120, 123, 122, 125 and 124,respectively, are shown in this Figure).

DETAILED DESCRIPTION OF THE INVENTION

Figure 1:
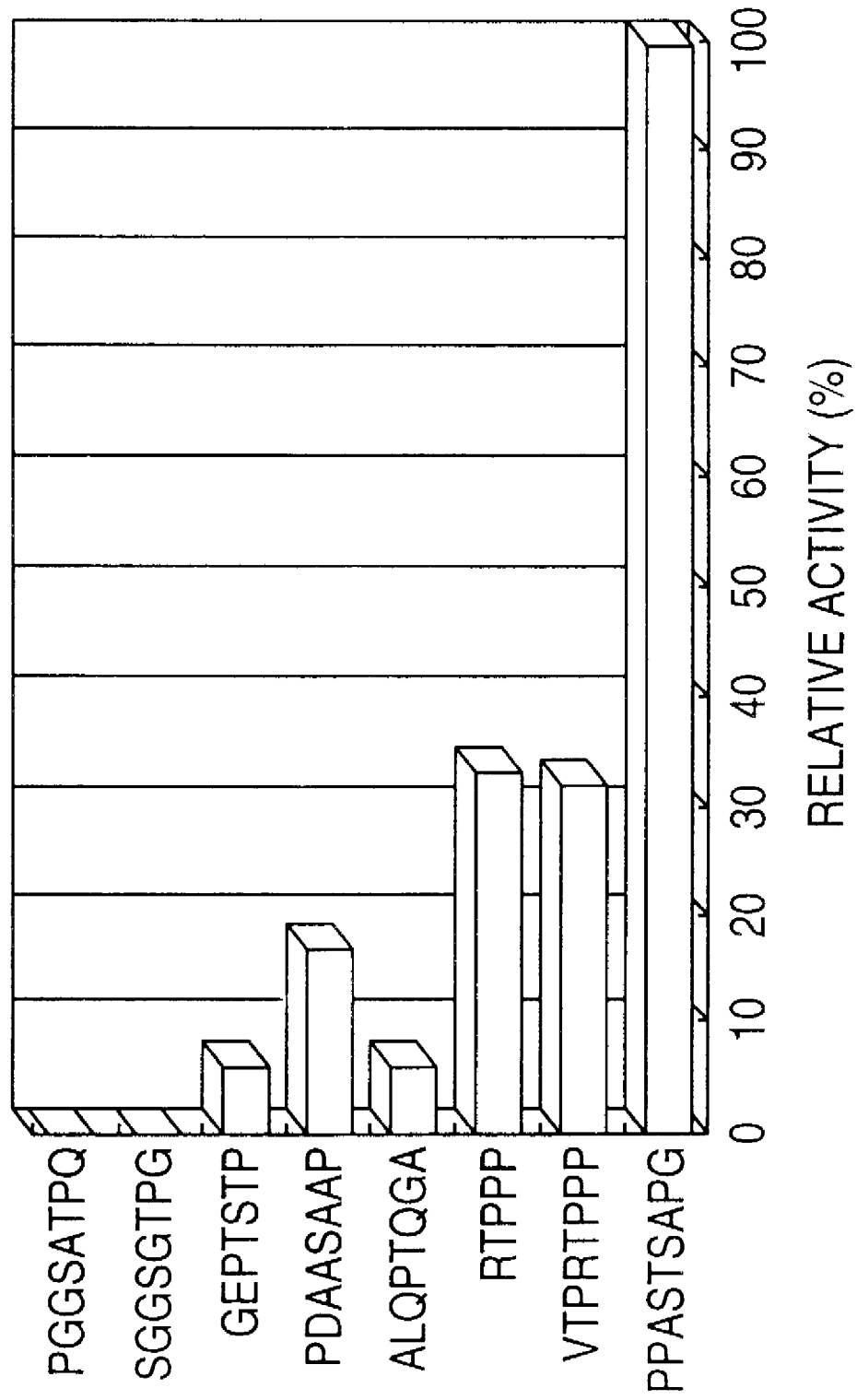
FIG. 1 is a graph showing the GalNAc acceptor activity of various peptides (SEQ ID NOS:1–8 are shown in this Figure).

Arabic numerals prefixed by "+" or "−" herein represent a position of an amino acid in a peptide. The position of amino acid where a sugar chain is transferred is called Position 0 and the positions on the N-terminal side and those on the C-terminal side are referred to as Positions −1, −2 and −3 and Positions +1, +2 and +3 in order.

Amino acids are herein represented by the known respective single character codes as shown below.

G: glycine
A: alanine
V: valine
L: leucine
I: isoleucine
S: serine
T: threonine
D: aspartic acid
E: glutamic acid
N: asparagine
Q: glutamine
K: lysine
R: arginine
C: cysteine
M: methionine
F: phenylalanine
Y: tyrosine
W: tryptophan
H: histidine
P: proline According to the first aspect of the present invention, a peptide represented by formula (I) is provided. The peptide having a sequence represented by formula (I) functions efficiently as a substrate for enzyme O-GalNAc T. In other words, it shows a high GalNAc acceptor activity. Therefore, GalNAc can be efficiently introduced into the peptide by reacting the peptide with UDP-GalNAc in the presence of O-GalNAc T. In this context, GalNAc is introduced to T or S at X(0).

GalNAc can be also introduced into a protein efficiently by reacting the peptide with UDP-GalNAc in the presence of O-GalNAc T, wherein the protein includes the peptide sequence represented by formula (I). Thus, according to the present invention, there is also provided a protein including a peptide sequence represented by formula (I).

A glycoprotein with mucin type sugar chains can be efficiently produced by secretory expressing a protein including a peptide sequence represented by formula (I) in an eucaryotic cell.

According to the preferred embodiment of the present invention, there is provided a protein or peptide of formula (I) having a high degree of GalNAc acceptor activity wherein X(1) and (3) represent P or A and either one of them is P.

According to another preferred embodiment of the present invention, there is provided a sequence having a high degree of GalNAc acceptor activity represented by the following formula (Ia):

$$X(-1)\text{-}X(0)\text{-}P\text{-}X(2)\text{-}P \qquad (Ia)$$

where X(−1), X(0) and X(2) are as defined above.

In this embodiment, X(−1) preferably represents an amino acid selected from Y, A, W, S, G, V, F, T and I and X(2) preferably represents an amino acid selected from A, P, C, K, R, H, S, M, T, Q, V, I, L and E.

According to another preferred embodiment of the present invention, there is provided a sequence showing a high degree of GalNAc acceptor activity represented by the following formula (Ib):

$$X(-1)\text{-}X(0)\text{-}X(1)\text{-}X(2)\text{-}P \qquad (Ib)$$

where X(-1), X(0), X(1) and X(2) are as defined above.

In this embodiment, X(-1) preferably represents an amino acid selected from Y, A, P, W, S, G, V, F, T and I and X(2) preferably represents an amino acid selected from A, P, C, K, R, H, S, M, T, Q, V, I, L and E. More preferably, X(-1) represents A or P, and X(1) and X(2) represent A.

According to another embodiment of the present invention, there is provided a sequence showing a high degree of GalNAc acceptor activity represented by the following formula (Ic):

$$X(-1)\text{-}X(0)\text{-}P\text{-}X(2)\text{-}X(3) \qquad (Ic)$$

where X(-1), X(0), X(2) and X(3) are as defined above.

In this embodiment, X(−1) preferably represents an amino acid selected from Y, A, P, W, S, G, V, F, T and I and X(2) preferably represents an amino acid selected from A, P, C, K, R, H, S, M, T, Q, V, I, L and E. More preferably, X(-1) represents A or P, and X(2) and X(3) represent A.

The peptide or protein represented by formulae (Ia) and (Ib) is preferable.

According to another preferred embodiment of the present invention, X(0) represents T. In some cases, when X(0) is T, the GalNAc acceptor activity is more than about 50 times greater than its counterpart when X(0) is S.

According to another preferred embodiment of the present invention, when one or two amino acids exist away from X(-1) on the N-terminal side, each of the amino acids is preferable A, P, G, E, Q, T, R or D. When one or more amino acids exist away from X(3) on the C-terminal side, they may be any amino acids.

While a peptide or amino acid according to the invention may be either an L- or D-isomer, it is preferably an L-isomer. In particular, the amino acid of X(2) is preferably an L-isomer.

Specific examples of a peptide sequence represented by formula (I) include the following. A protein according to the invention preferably contains a peptide sequence selected from the following.

ATPAP (SEQ ID NO:31)
AATPAP (SEQ ID NO:32)
AAATPAA (SEQ ID NO:16)
AAATAAP (SEQ ID NO:18)
PAATAAP (SEQ ID NO:20)
APATAAP (SEQ ID NO:21)
AAPTAAP (SEQ ID NO:28)
AAATAPP (SEQ ID NO:24)
PAATPAP (SEQ ID NO:25)
APATPAP (SEQ ID NO:26)
AAXaTPXbP where Xa and Xb represent any amino acid provided that either Xa or Xb represents A, and

AAATPAPXC where Xc represents any amino acid.

A protein or peptide according to the invention may be synthesized by means of a technique of genetic engineering or by chemical synthesis.

According to another aspect of the present invention, there is provided a method of introducing mucin type sugar chains into a protein or peptide.

The introduction of sugar or sugar chains into a protein or peptide according to the present invention is conducted in a manner as described below. When the introduction is conducted in vitro, a protein or peptide according to the invention is prepared and reacted with UDP-GalNAc as a sugar donor in the presence of O-GalNAc T preferably in a buffer solution containing MnCl$_2$ or Triton X-100. The concentrations of the sugar donor and the sugar acceptor may be used without limitation up to a saturated state. While the enzyme O-GalNAc T may also be used without limitation, it is preferably used at the rate of about 10 mU to 10 U per 1 milliliter of the reactive solution. The pH of the buffer solution is preferably about 7. The use of imidazole-hydrochloric acid buffer solution having a pH value of about 7.2 is preferable. The reaction is conducted in general at 25° to 37° C. and completes in several minutes to tens of several hours depending on the conditions.

According to the present invention, sugar chains may be introduced into a protein or peptide by means of a biosynthesis pathway of eucaryotic cells having the enzyme of O-GalNAc T. More specifically, a protein or peptide having mucin type sugar chains can be obtained by secretory expressing a protein or peptide according to the present invention in an eucaryotic cell having the enzyme of O-GalNAc T. It may be safe to presume that the introduced sugar chain is bound to amino acid X(0) of the sequence represented by formula (I). Preferable examples of eucaryotic cells having O-GalNAc T includes animal cells such as COS7, COS1, BHK, C127 and CHO and insect cells such as Sf9 and Sf21.

In the present invention, when sugar chains are introduced by means of a biosynthesis pathway of eucaryotic cells, the protein has to be secreted out of the cells. Therefore, when the protein or peptide into which sugar chains are to be introduced can not be easily secreted out of the eucaryotic cell, it is preferable that the peptide is expressed as a precursor having a signal peptide attached thereto. By the secretion of the protein from the cell, sugar chains can be introduced and the intended protein can be obtained as mature protein.

Known available technique of genetic engineering can be used for secretory expressing a protein or peptide according to the present invention. It may be obvious to one skilled in the art that a protein or peptide having a sequence as represented by formula (I) can be expressed in cells as described above. A sequence represented by formula (I) can be inserted or added to a desired position of a protein or peptide, or can replaced at the desired position of the protein or peptide with a sequence represented by formula (I).

More specifically, according to the present invention, there is provided a method of preparing a protein or a peptide having a mucin type sugar chain comprising the steps of:

transforming an eucaryotic cell with a DNA coding for a protein or peptide according to the invention; and expressing the protein or peptide in the transformed cells and secreting the protein or peptide from the eucaryotic cell.

According to another aspect of the invention, there is provided a method of introducing a mucin type sugar chain into a desired position of a protein or peptide of interest comprising the steps of:

inserting or adding a DNA coding for a sequence represented by formula (I) into a position which is in a DNA coding for the protein or peptide of interest and is corresponding to the position where a mucin type sugar chain is intended to be introduced, or replacing a partial DNA fragment including the position with a DNA coding for a sequence represented by formula (I), thereby a DNA coding for a protein or peptide containing the DNA coding for the sequence represented by formula (I) is obtained;

transforming an eucaryotic cell with the DNA obtained in the above step; and expressing the protein or peptide in the transformed cell and secreting the protein or peptide having a mucin type sugar chain from the cell.

Preferably, the DNA coding for a protein or peptide containing the DNA coding for the sequence represented by formula (I) is preferably in the form of a vector. More preferably, it is in the form of an expression vector including various sequences for promoting or regulating the expression. Without undue experiment, one skilled in the art can select a vector suitable for the present invention from a group of vectors used in the field of genetic engineering and also can construct an expression vector which are useful in the present invention. As described above, an eucaryotic cell to be used in the present invention may be a cell having O-GalNAc T. In addition, vectors that can be used for such cells and can suitably be used in the present invention are known. (See, Molecular Cloning [J. Sambrook et al., Cold Spring Harbor Laboratory Press (1989)] and Baculovirus Expression Vectors: a laboratory manual [D. R. O'Reilly et al., W. H. Freeman and Company (1992).])

Thus, according to the present invention, there is provided a DNA sequence coding for a sequence represented by formula (I) along with a DNA sequence coding for a protein or peptide including a sequence represented by formula (I).

A glycoprotein or glycopeptide produced by a method according to the present invention can be easily isolated and purified from the solution after the reaction by using a known appropriate technique. The techniques include affinity column chromatography, gel filtration column chromatography and reversed phase column chromatography. The reaction product can be collected by condensation and/or lyophilization.

With a method of introducing sugar chains according to the present invention, a mucin type sugar chain can be introduced into a desired position of a protein or peptide of which structures are known. Furthermore, a sequence represented by formula (I) consisting of only five amino acids. With this short sequence, a sugar chain can be highly probably introduced into a protein or peptide having such a short sequence. Thus, according to the present invention, a protein or peptide chain can advantageously be modified to be linked with mucin type sugar chains without affecting the structure of the protein or peptide of which structures are already known. A technique according to the present invention will find a wide variety of applications in the pharmaceutical industry and other industries.

In addition, a glycoprotein or glycopeptide prepared according to the present invention may be used as a substrate for a variety of glycosidases and glycosyltransferases. Therefore, the protein can be used for detecting useful enzymes. For instance, it can advantageously be used for preparing substrates of enzymes that can take part in the formation of mucin type sugar chains. More specifically, AAAT($\alpha$-GalNAc)PAP that can be obtained by using AAATPAP (SEQ ID NO:23) can be used for detecting and measuring $\alpha$-N-acetylgalactosaminidase or UDP-Gal: GalNAc-polypeptide $\beta$1,3-galactosyltransferase in samples that may be derived from living things including microorganisms, insects, animals, plants and their cell culture solutions.

Furthermore, a carrier having peptides can be prepared by providing a peptide according to the present invention and thereafter binding it to an activated carboxylagarose or cyanogen bromide activated agarose. Such a carrier having peptides can advantageously be used for purifying mucin type glycosyltransferase such as O-GalNAc T.

EXAMPLES

The present invention will be described in detail by way of examples, which by no means limits the scope of the invention.

In the following examples, the purification of O-GalNAc T, the peptide synthesis and the measurement of the GalNAc acceptor activity of the synthesized peptide were carried out in a manner as described below.

Purification of O-GalNAc T

O-GalNAc T derived from colostrum of cow was purified by a method reported by A. Elhammer et al. [J. Biol. Chem., Vol.261, pp.5249–5255 (1986)].

More specifically, an about 4.8 liters of colostrum of cow was centrifuged to remove butter component and then subjected to an ultracentrifugation. A 800 milliliters of glycerol was added to the obtained 3.2 liters solution to produce a crude enzyme solution, which was subsequently subjected to a 4-step purifying process including DEAE-Sephacel column chromatography, ultrafiltration and apomucin-Sepharose 4B column chromatography I and II to produce highly but partially purified preparations.

Synthesis of Peptide

Peptides were synthesized by Fmoc solid phase method [N. Izumiya et al., Bases and Experiments on Peptide Synthesis, Maruzen, 1985] with PS3 Automatic Peptide Synthesizer available from Protein Technologies. The synthesized peptide was analyzed in structure and quantified by a mass spectroscopy (Mass Analyzer API III: available from Parkin Elmer) and amino acid composition analysis (Amino Acid Composition Analyzer JLC-300: available from Nippon-Denshi).

Measurement of GalNAc Acceptor Activity of Peptide

The GalNAc acceptor activity of peptide was determined by a method proposed by J. M. Cottrell et al. [Biochem. J., Vol.283, pp.299–305 (1992)] and A. P. Elhammer et al. [J. Biol. Chem., Vol.268, pp.10029–10038 (1993)].

More specifically, 50 μl of a reaction solution (50 mM Imidazole-HCl (pH 7.2), 10 mM MnCl$_2$, 0.5% Triton X-100, 150 μM UDP-[$^3$H]GalNAc) containing 100 nmol of a synthesized peptide and 0.5 to 500 mU of partially purified O-GalNAc T derived from colostrum of cow was prepared and warmed appropriately at 37° C. for 30 minutes to 5 hours. The reaction was terminated by adding 50 μl of 100 mM of EDTA and, subsequently, put into an 1 ml ion exchange column (AG1-X8, Cl$^-$form: available form Japan Bio-Rad laboratory) and the reaction product was eluted with 2.5 ml of water. A 10 ml of a cocktail for liquid scintillation counters (Atomlight: available from Dupont) was added to the eluted fraction and measured radioactivity by a liquid scintillation counter for 2 minutes.

The GalNAc acceptor activity was expressed in terms of the initial reaction velocity relative to a peptide PPASTSAPG (SEQ ID NO:8) which was set to 100%.

Example 1

GalNAc Transfer into Various Peptides

The GalNAc acceptor activity of each of the peptides listed in FIG. 1 was measured.

These peptide sequences are either those derived from mucin type glycoproteins or those that are already known as GalNAc acceptors with O-GalNAc T. More specifically, PGGSATPQ, SGGSGTPG, GEPTSTP, PDAASAAP and ALQPTQGA (SEQ ID NO:1–5) are respectively derived from mucin of swine submaxillary gland, mucin of sheep submaxillary gland, bovine κ-casein, human erythropoietin and human granulocyte colony stimulating factor. RTPPP and VTRTPPP (SEQ ID NO:6 and 7) are derived from bovine myelin and J. D. Young et al. reported that GalNAc was transferred to these peptides [Biochemistry; Vol.18, pp.4444–4448 (1979)]. With regard to PPASTSAPG (SEQ ID NO:8), A. P. Elhammer et al. reported that GalNAc was transferred to this peptide [J. Biol. Chem.; Vol.268, pp.10029–10038 (1993)].

The results are shown in FIG. 1. As seen from FIG. 1, PPASTSAPG (SEQ ID NO:8), which may be an ideal peptide sequence according to A. P. Elhammer et al., showed the highest activity of all, followed by RTPPP and VTRTPPP (SEQ ID NO:6 and 7). On the other hand, all the peptide sequences derived from natural mucin type proteins showed a low activity. And, no GalNAc transfer was observed in the peptide sequences derived respectively from the submaxillary gland mucins.

Example 2

Influence of amino acids, threonine and serine, at the binding site of a sugar chain A mucin type sugar chain is bound to threonine or serine. Therefore, the preference of the amino acids to a GalNAc transfer was tested for comparison.

Among the peptides listed in Example 1, the peptides derived from erythropoietin and myelin which contain only one serine or threonine residue were used. They clearly showed a GalNAc transfer more than any other peptides used in Example 1. Then, PDAATAAP and PDAASAAP (SEQ ID NO:12 and 4 respectively) derived from erythropoietin and RTPPP and RSPPP (SEQ ID NOS:6 and 9, respectively) derived from myelin were prepared.

Figure 2:
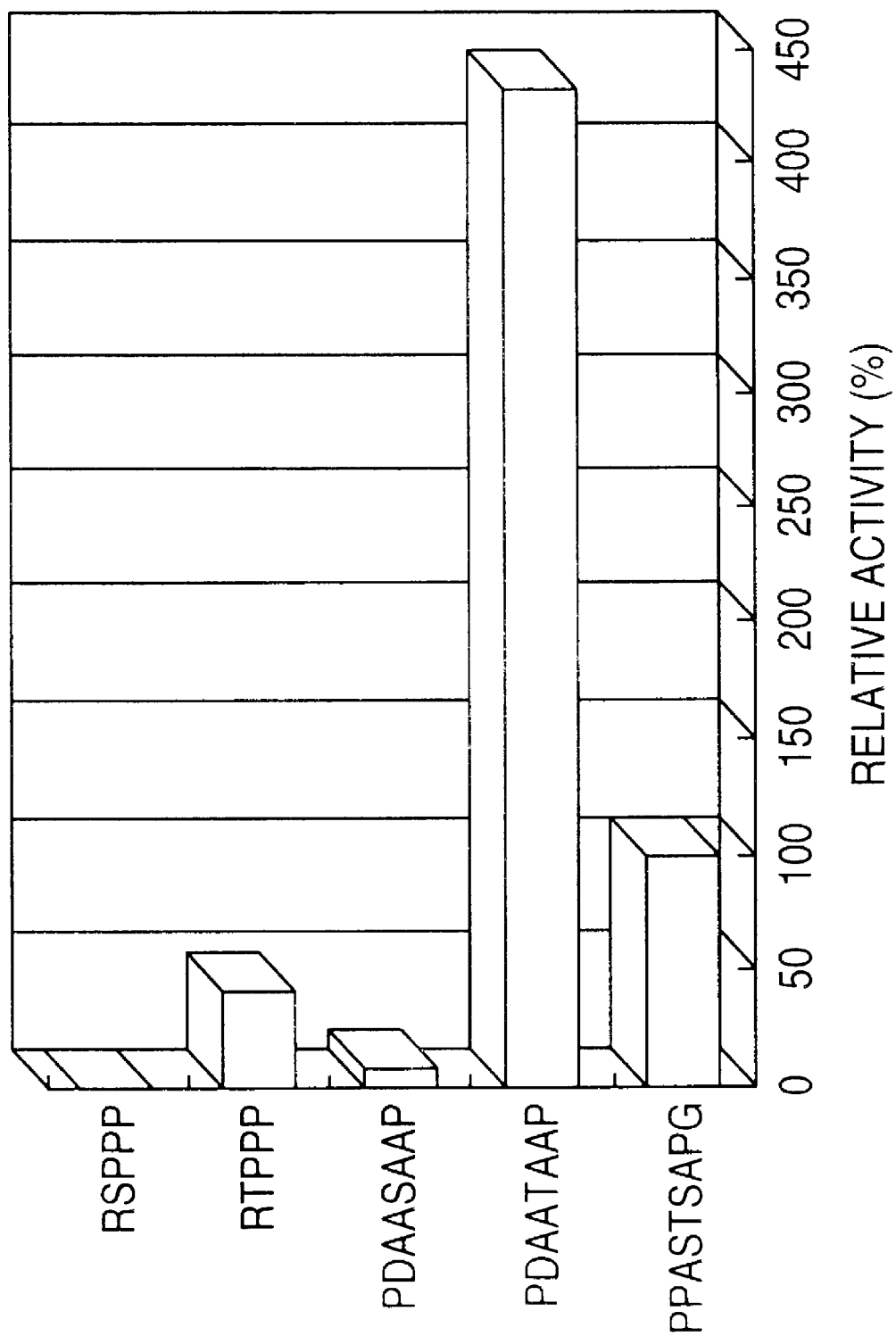
FIG. 2 is a graph showing which amino acid, T or S, to be suitable as the site for binding a sugar chain in GalNAc transfer.

FIG. 2 shows the results. As seen from FIG. 2, threonine was 40 to 50 times more active than serine in each case. PDAATAAP (SEQ ID NO:12) showed an activity level about 4 times higher than that of PPASTSAPG (SEQ ID NO:8) which showed the highest activity level in Example 1.

Example 3

GalNAc Transfer to Peptides Containing a Single Proline Residue

The influence of a proline residue in a peptide in the GalNAc transfer reaction was then examined, because proline was relatively frequently observed in the peripheral sequence of the amino acid where a mucin type sugar chain was bound and because each of the peptides that showed a high GalNAc acceptor activity in Examples 1 and 2 contained several proline residues. As the first step, a single proline residue was replaced with one alanine residue in AAATAAA (SEQ ID NO:19) to prepare various peptides and GalNAc acceptor activities of the peptides were compared. The prepared peptides were AAATAAA, PAATAAA, APATAAA, AAPTAAA, AAATPAA, AAATAPA and AAATAAP )SEQ ID NOS:19 and 13–18, respectively).

Figure 3:
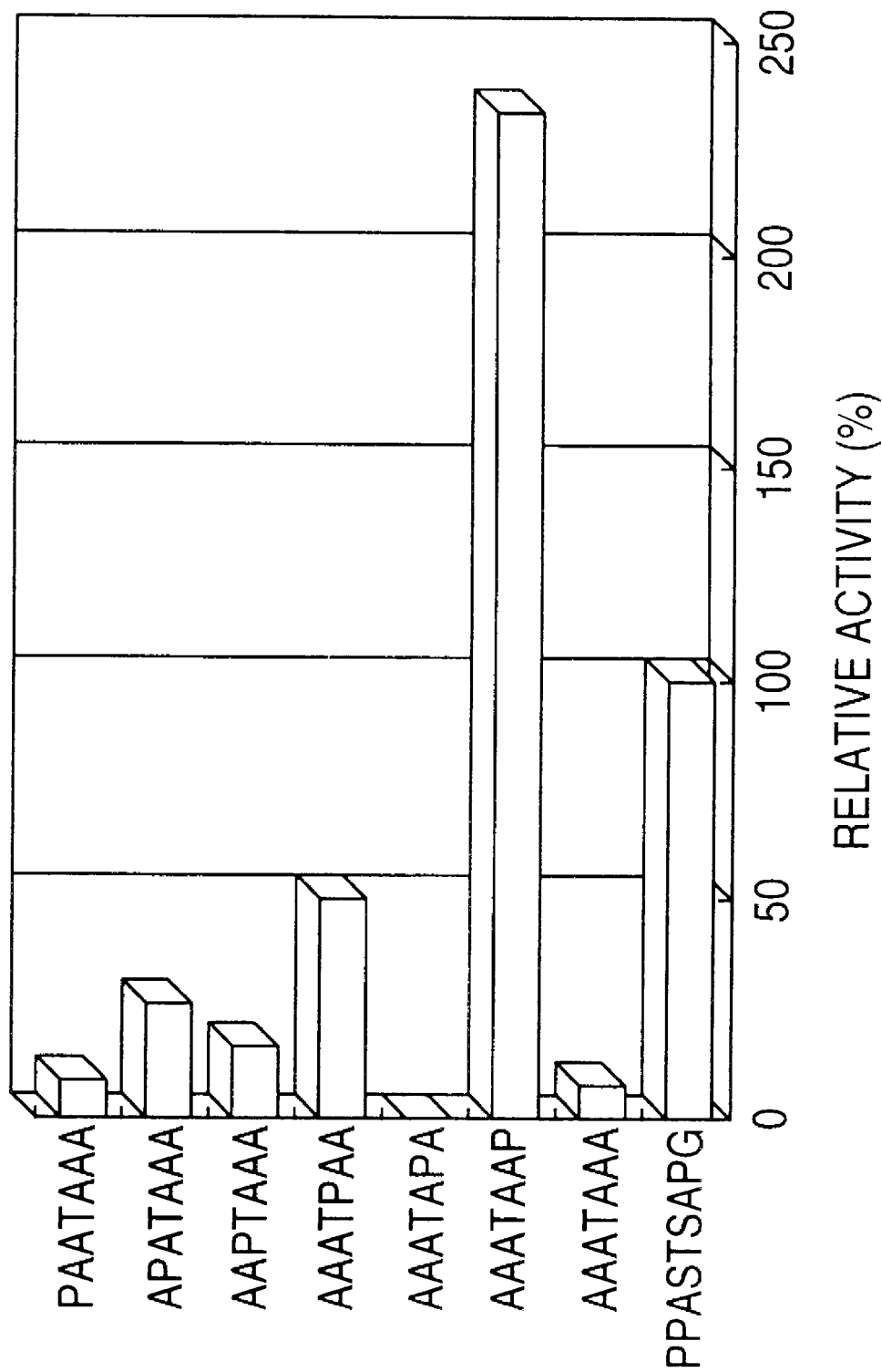
FIG. 3 is a graph showing the GalNAc acceptor activities of various peptides having a single proline residue (SEQ ID NOS:13–19 and 8, respectively, are shown in this Figure.

The GalNAc acceptor activity of each of the peptides is shown in FIG. 3. While AAATAAA (SEQ ID NO:19) scarcely showed any activity, AAATPAA and AAATAAP showed a significantly high level activity. Consequently, it was found that the existence of proline at Position +1 and +3, particularly at Position +3, is important for GalNAc acceptor activity. AAATAAP (SEQ ID NO:18) showed an activity level about twice as high as that of PPASTSAPG.

Example 4

GalNAc Transfer to Peptides Containing Two Proline Residues

The results of Example 3 showed that a significant effect can be produced by introducing a single proline residue into a specific site. Therefore, in this Example, a second proline residue was introduced to each alanine position of AAATAAP (SEQ ID NO:18) which showed the highest activity level in Example 3 in order to find out the effect of the second proline residue. The peptides prepared for comparing the GalNAc acceptor activities were AAATAAA, AAATAAP, PAATAAP, APATAAP, AAPTAAP, AAATPAP and AAATAPP (SEQ ID NOS:19, 18, and 20–24, respectively).

Figure 4:
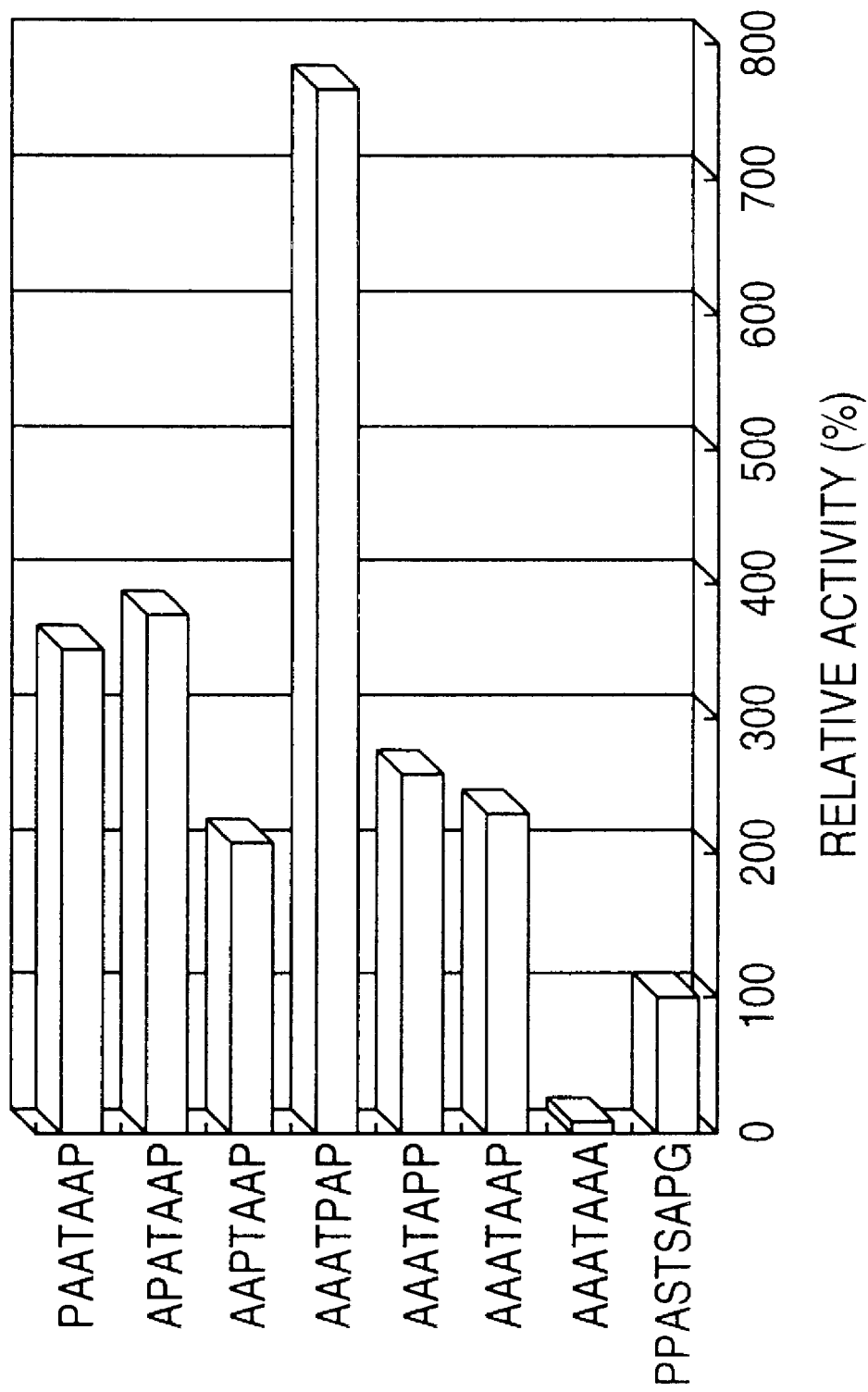
FIG. 4 is a graph showing the GalNAc acceptor activities of various peptides having two proline residues (SEQ ID NOS:20–24, 18–19 and 8, respectively, are shown in this Figure).

FIG. 4 illustrates the results. As seen from FIG. 4, AAATPAP showed a acceptor activity level about three times higher than that of AAATAAP (SEQ ID NO:18). This proves that the GalNAc transfer to peptide was synergistically promoted when two proline residues were provided at both Positions +1 and +3. AAATPAP (SEQ ID NO:23) showed an activity level about seven times as high as that of PPASTSAPG (SEQ ID NO:8). The effect of the proline at Position +3 remained stable even when the alanine residues at Positions −3, −2, −1 and +2 were switched to proline.

Example 5

GalNAc Transfer to Peptides Containing Three Proline Residues

As proved in Example 4, the two proline residues at Positions +1 and +3 in a peptide sequence greatly improves the GalNAc acceptor activity. In this Example, therefore, a third proline residue was introduced to each alanine position of AAATPAP in order to find out the effect of the third proline residue. The peptides prepared for comparing the GalNAc acceptor activities were AAATAAP, AAATPAP, AATPAP, APATPAP, AAPTPAP and AAATPPP (SEQ ID NOS:18, 23, 32, and 26–28, respectively).

Figure 5:
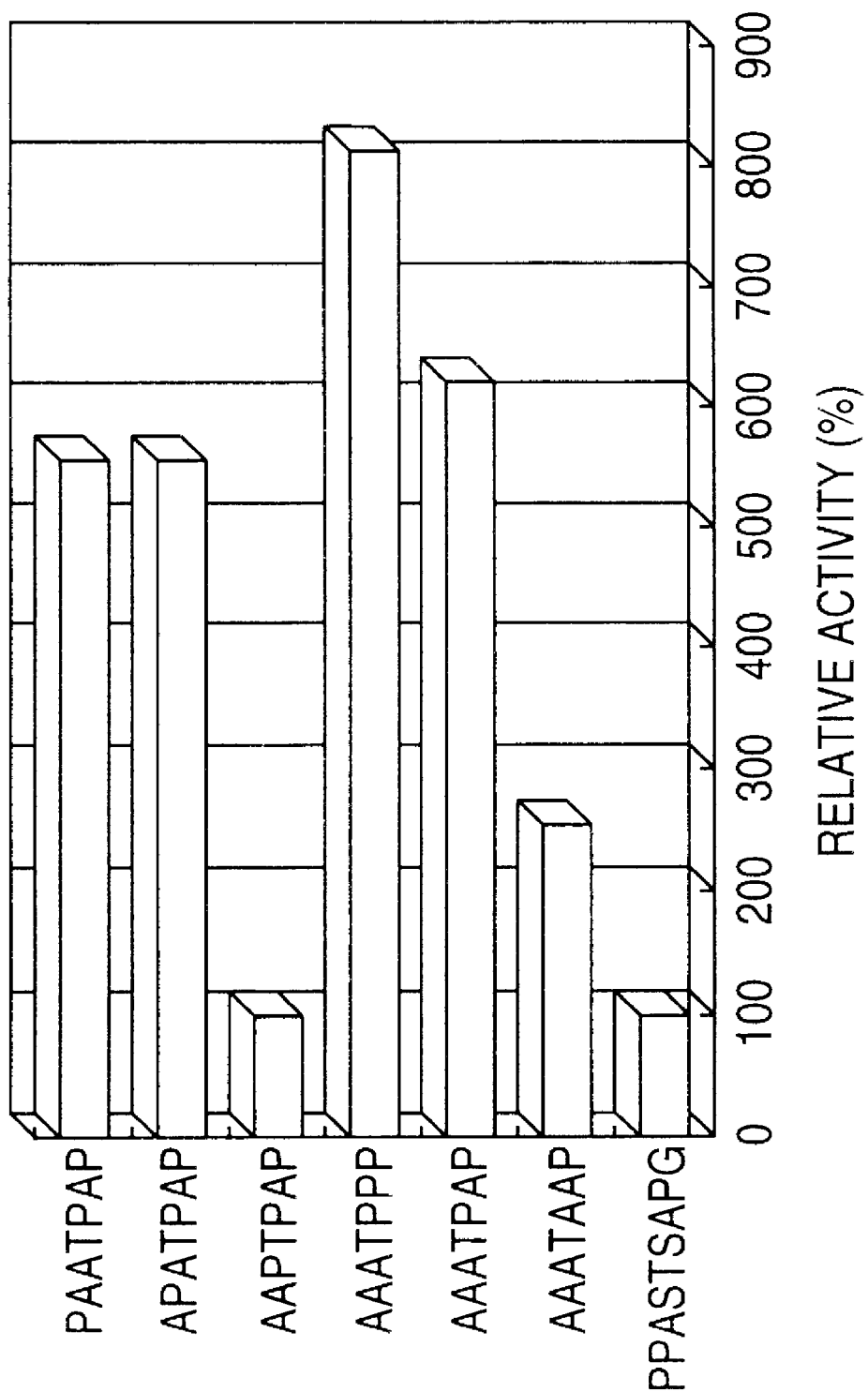
FIG. 5 is a graph showing the GalNAc acceptor activities of various peptides having three proline residues (SEQ ID NOS:25–28, 23, 18 and 8, are shown in this Figure).

FIG. 5 illustrates the results. As seen from FIG. 5, the GalNAc acceptor activity level did not significantly increase when a proline residue was introduced at a position other than +1 and +3. This clearly indicates that two proline residues at Position +1 and +3 are important for the GalNAc acceptor activity. While the third proline introduced into any of Positions −3, −2 and +2 did not show any significant change in the activity, the level decreased remarkably when it was introduced into Position −1. From these results, it indicates that the effect of the two proline residues at Positions +1 and +3 was not basically affected by the amino acids at the remaining positions. It also suggests that, when proline residues which are unique amino acids are located on the both sides (−1 and +1) of the threonine to which GalNAc is transferred, a unusual peptide structure may be formed to reduce the activity.

In view of the results of Examples 3 to 5, it is clear that the requirement for a peptide to accept GalNAc is not that one or more proline residues exists at random but that they should be located at specific positions. Further, the requirement for a peptide to have higher GalNAc acceptor activity is not that the number of proline residues around serine or threonine to which GalNAc is transferred is merely increased but that they are located specific and limited positions.

Example 6
GalNAc Transfer to Peptides with Different Numbers of Amino Acids on the N-terminal Side of the Binding Site In view of the results of Examples 3 to 5, it is also clear that the amino acids located at Positions from −3 to −1 of the N-terminal side do not significantly affect the GalNAc acceptor activity regardless if they are alanine or proline. Therefore, peptides with different numbers of amino acid residues on the N-terminal side were prepared and tested for GalNAc acceptor activity in order to find out if the amino acid residues at Positions from −3 to −1 were really necessary for GalNAc acceptor activity. The peptides prepared were AAATPAP, AATPAP, ATPAP and TPAP (SEQ ID NOS:23, 32, 31, and 30, respectively).

Figure 6:
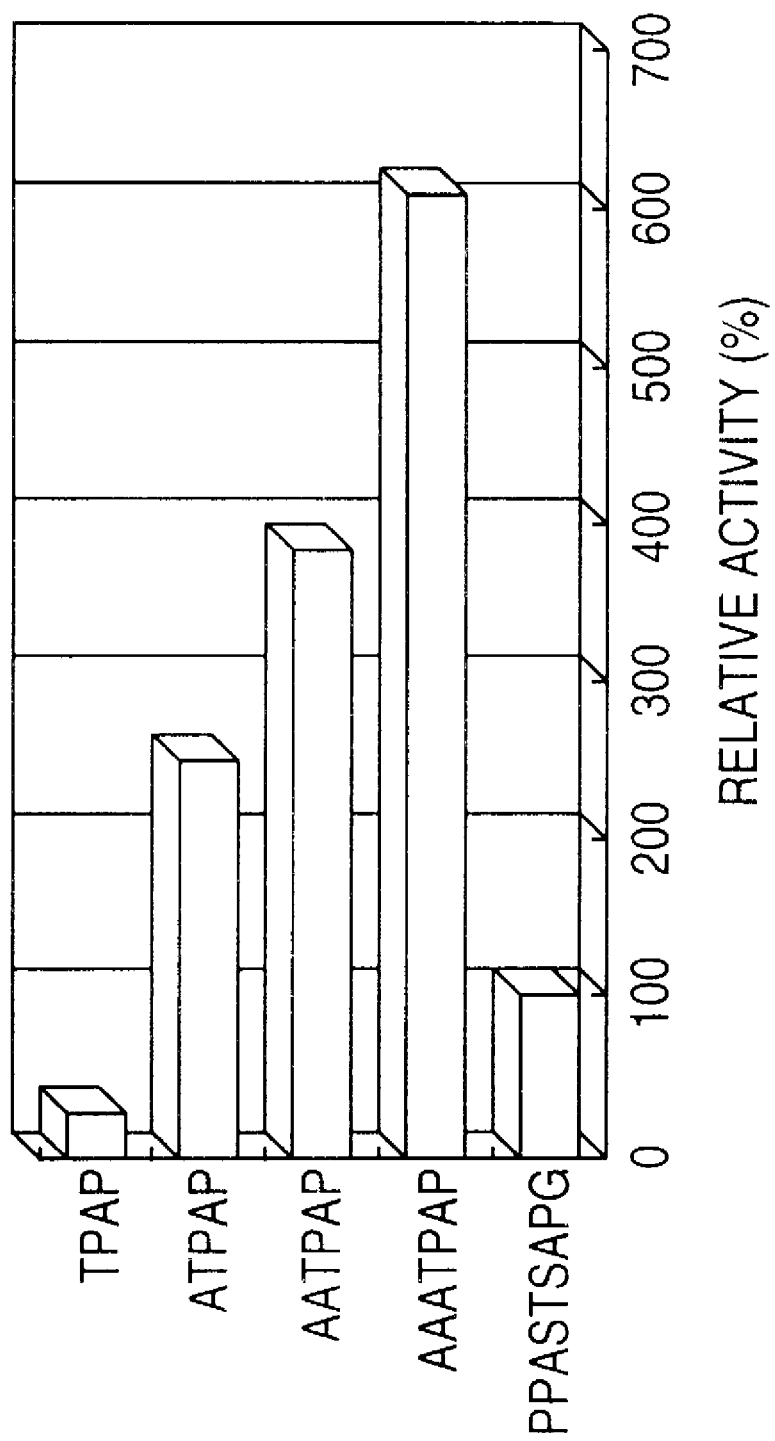
FIG. 6 is a graph showing the GalNAc acceptor activities of various peptides having different numbers of N-terminal amino acid residues (SEQ ID NOS:30–32, 23 and 8, respectively, are shown in this Figure).

FIG. 6 illustrates the results. As seen from FIG. 6, while ATPAP (SEQ ID NO:31) showed a high GalNAc acceptor activity but that of TPAP (SEQ ID NO:30) was dramatically low. Thus, it was proved that, in order to obtain a high GalNAc acceptor activity, at least one amino acid residue is required on the N-terminal side of threonine or serine to which GalNAc is transferred. At the same time, it was also found that the presence of two or more amino acids on the N-terminal side of threonine is preferable but not essential, because the GalNAc acceptor activity increases depending on the number of amino acids on the N-terminal side up to three amino acid residues.

Example 7
GalNAc Transfer to Peptides with Different Amino Acids at Position +2

The results of Example 6 exhibited that peptide sequences having ATPAP in common show a high level GalNAc acceptor activity. This peptide has two proline residues. Since proline has a unique structure among various amino acids, it was quite probable that the amino acid residue located between the two proline residues, at Position +2, could significantly affect the peptide structure. Thus, 20 peptides having different amino acids at Position +2 were prepared and compared for GalNAc acceptor activity. The prepared peptides were AAATPAP, AAATPPP, AAATPCP, AAATPKP, AAATPRP, AAATPHP, AAATPSP, AAATPMP, AAATPTP, AAATPQP, AAATPVP, AAATPIP, AAATPLP, AAATPEP, AAATPGP, AAATPYP, AAATPWP, AAATPFP, AAATPNP and AAATPDP (SEQ ID NOS:23, 28, and 33–50, respectively).

Figure 7:
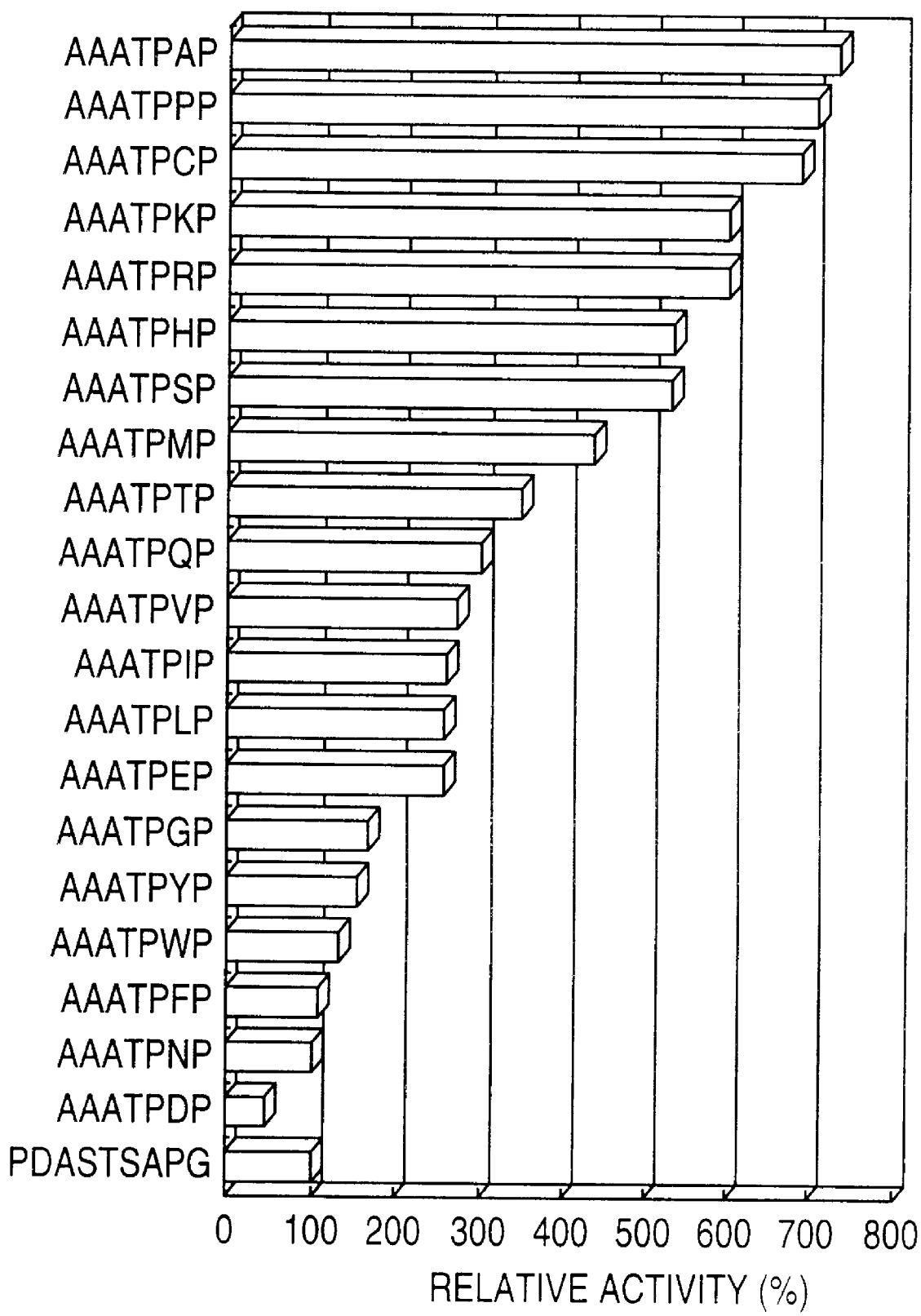
FIG. 7 is a graph showing the GalNAc acceptor activities of various peptides, where X(2) is substituted with various amino acids (SEQ ID NOS:32, 28, 33–50 and 8, respectively, are shown in this Figure).

FIG. 7 illustrates the results. As seen from FIG. 7, the peptide shows a high GalNAc acceptor activity generally if proline exists at Position +1 and +3 regardless of a side chain of the amino acid at Position +2. On the other hand, the activity may vary depending on the side chain of the amino acid at Position +2. In particular, each peptide having alanine, proline, cysteine, lysine, arginine, histidine, serine, methionine, threonine, glutamine, valine, isoleucine, leucine or glutamic acid shows a higher GalNAc acceptor activity than the peptide having glycine, tyrosine, tryptophan, phenylalanine, asparagine or aspartic acid. The results prove that the amino acid at Position +2 preferably has a relatively small side chain and a positive charge.

Example 8
GalNAc Transfer to Peptides with Optical Isomers of Amino Acids at Position +2

The results of Example 7 suggest that the side chain of the amino acid at Position +2 of the basic peptide sequence, ATPAP (SEQ ID NO:31), having the high GalNAc acceptor activity, might affect on the activity. Thus, with regard to the alanine at Position +2, D- and L-optical isomers were prepared and compared for GalNAc acceptor activity. The prepared peptides were PAATAAP, APATAAP, AAPTAAP and AAATPAP (SEQ ID NOS:20–23), for which D- and L-optical isomers of alanine were formed at Position +2.

Figure 8:
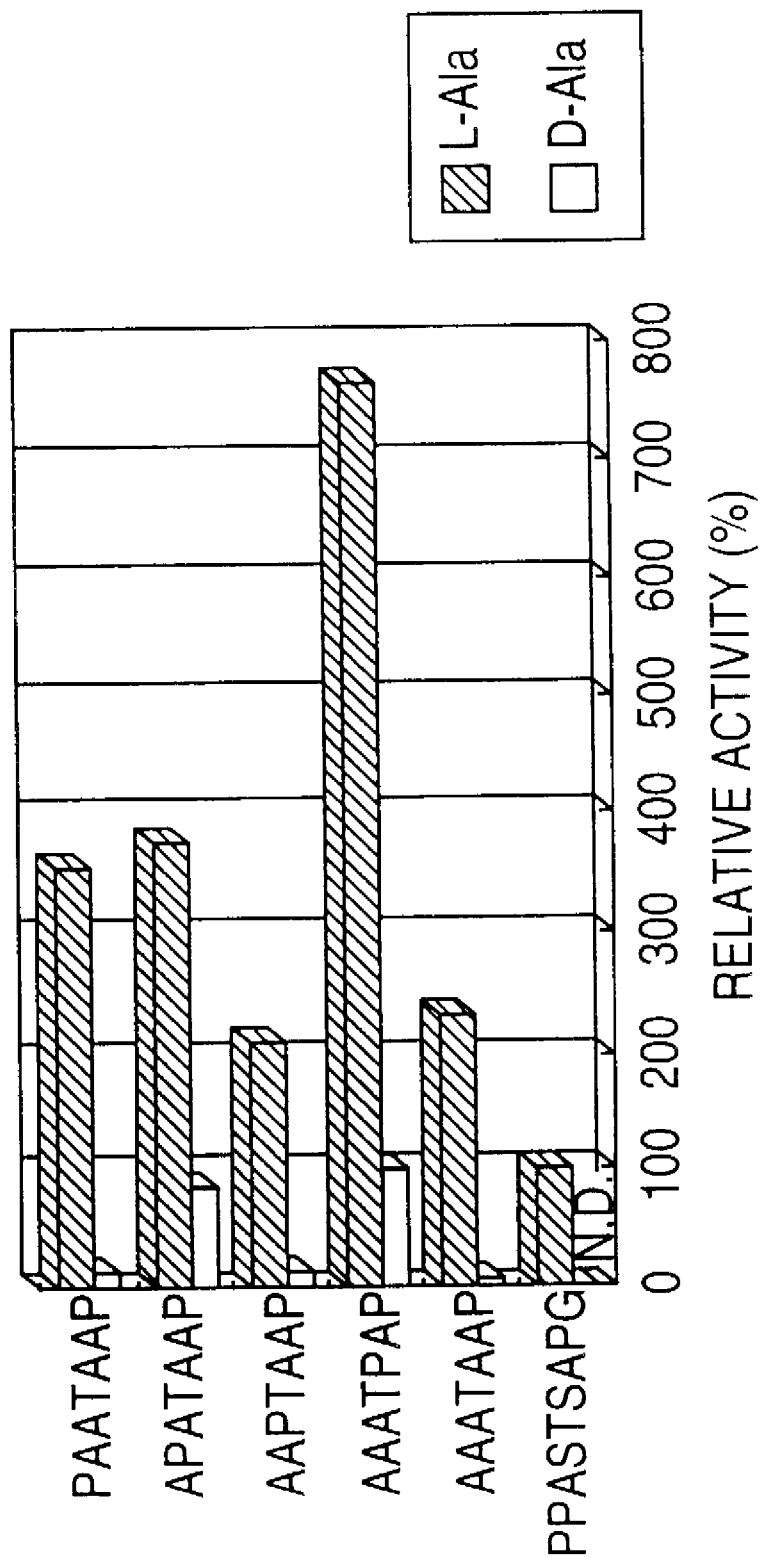
FIG. 8 is a graph showing the GalNAc acceptor activities of various peptides, where X(2) is substituted with an L- or D-optical isomer (SEQ ID NOS:20–23, 18 and 8, respectively, are shown in this Figure).

FIG. 8 shows the results. As seen from FIG. 8, the L-isomers generally showed a higher activity than the D-isomer counter parts, although the latter also provided a high level of activity. Consequently, it was confirmed that the amino acid at Position +2 may be D-isomer that is optically symmetric to its natural counterpart and the side chain of the amino acid residue at Position +2 has little significance in terms of GalNAc acceptor activity.

Example 9
GalNAc Transfer to Peptides with Different Amino Acids at Position −1

The results of Example 6 showed that the amino acid at Position −1 is important for GalNAc acceptor activity. Therefore, 20 peptides having different amino acids at Position −1 were prepared and compared for GalNAc acceptor activity. The prepared peptides were AAYTPAP, AAATPAP, AAWTPAP, AASTPAP, AAGTPAP, AAVTPAP, AAFTPAP, AATTPAP, AAITPAP, AAHTPAP, AAMTPAP, AAQTPAP, AACTPAP, AANTPAP, AAPTPAP, AALTPAP, AARTPAP, AAETPAP, AADTPAP and AAKTPAP (SEQ ID NOS:51, 13, 52–63, 27, and 64–68, respectively).

Figure 9:
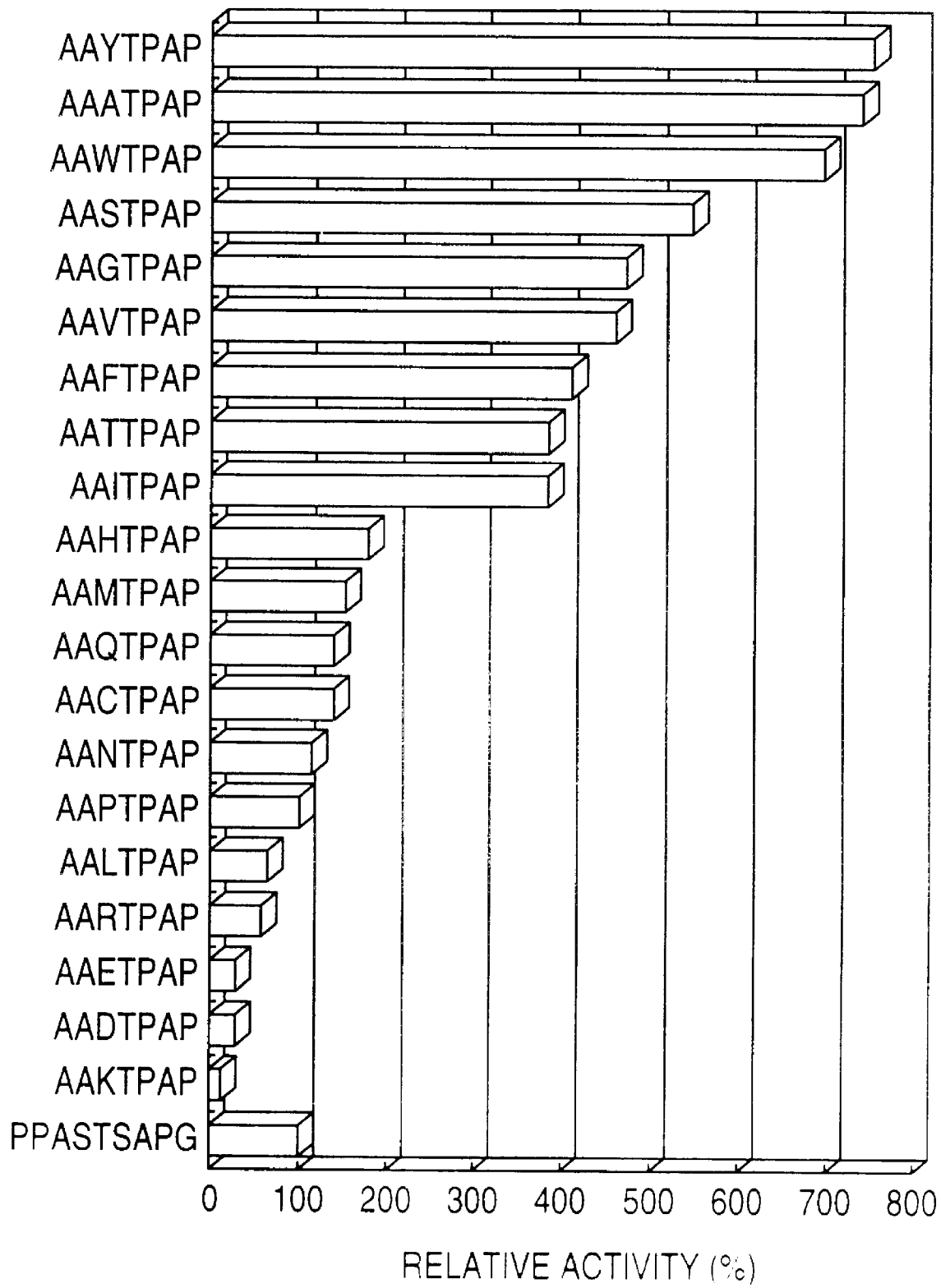
FIG. 9 is a graph showing the GalNAc acceptor activities of various peptides, where X(-1) is substituted with various amino acids (SEQ ID NOS:51, 23, 52–63, 27, 64–68 and 8, respectively, are shown in this Figure).

FIG. 9 illustrates the results. As seen from FIG. 9, the peptides generally show a high GalNAc acceptor activity level if proline exists at +1 and +3 regardless of the side chain of the amino acid at Position −1. However, the activity level may vary relatively significantly depending on the side chain of the amino acid at Position −1. In particular, each peptide having tyrosine, alanine, tryptophan, serine, glycine, valine, phenylalanine, threonine or isoleucine shows a higher GalNAc acceptor activity than that having histidine, methionine, glutamine, cysteine, asparagine, proline, leucine, arginine, glutamic acid, aspartic acid or lysine. These results show that the amino acid at Position −1 is not charged but aromatic, although the size of the side chain has little to do with the GalNAc acceptor activity.

Example 10
GalNAc Transfer to Peptides with Different Amino Acids at Position +4

The results of Examples 1 through 9 showed that the motif of peptide sequence having a high GalNAc acceptor activity level is X(-1)-T-P-X(2)-P, where X(-1) and X(2) represent any amino acid. In this motif, the proline at Position +3 is important and the C-terminal side should not be made shorter than it. On the other hand, the significance of the amino acid at Position +4 remains still unknown. Therefore, 20 peptides having different amino acids at Position +4 were prepared and compared for GalNAc acceptor activity. The prepared peptides were AAATPAP, AAATPAPG, AAATPAPQ, AAATPAPE, AAATPAPA, AAATPAPN, AAATPAPD, AAATPAPR, AAATPAPC, AAATPAPI, AAATPAPV, AAATPAPS, AAATPAPK, AAATPAPY, AAATPAPL, AAATPAPT, AAATPAPW, AAATPAPM, AAATPAPP, AAATPAPF and AAATPAPH (SEQ ID NOS:23, and 69–88, respectively).

Figure 10:
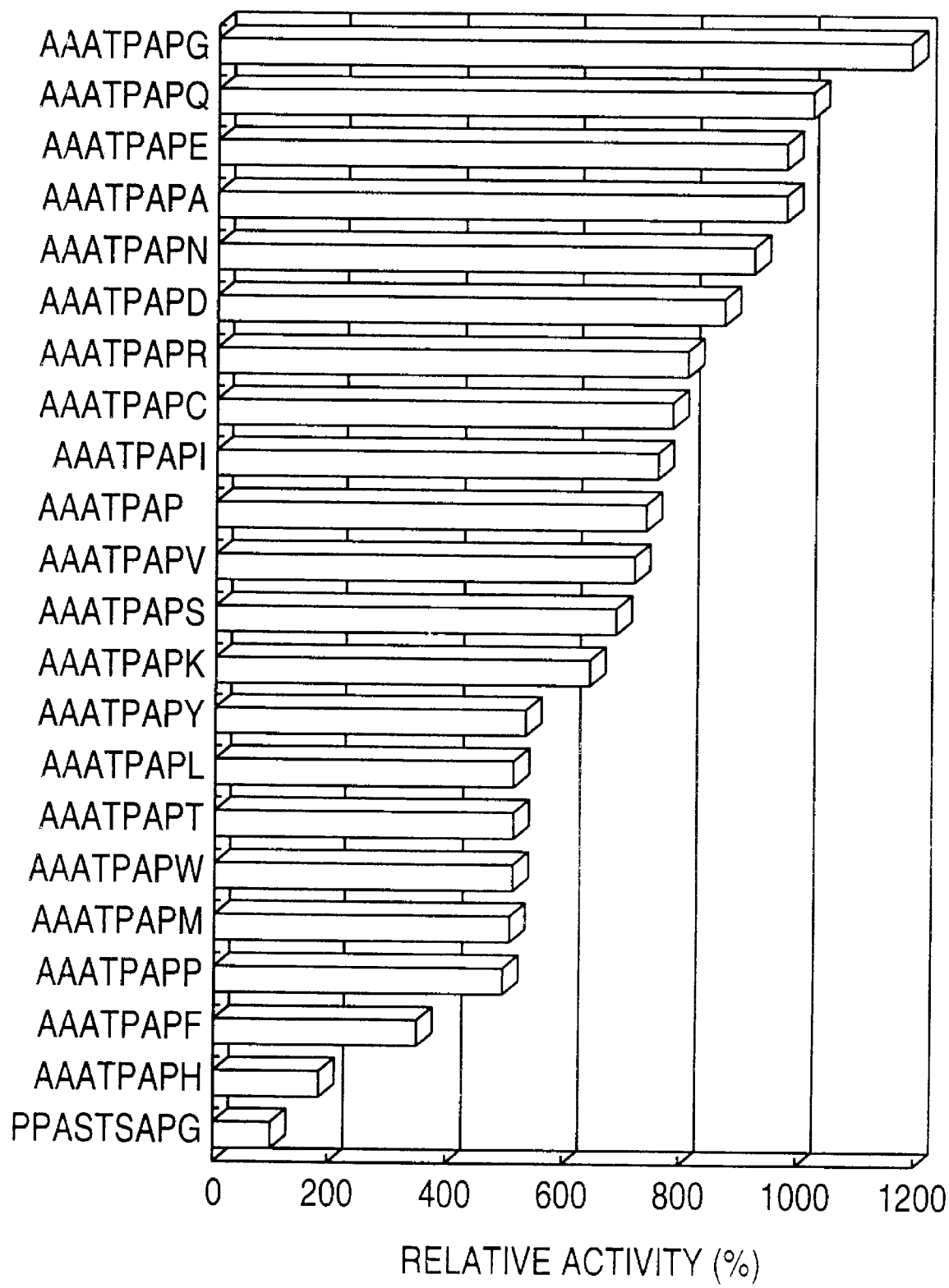
FIG. 10 is a graph showing the GalNAc acceptor activities of various peptides, where various amino acids are added to Position +4 (SEQ ID NOS:69–77, 23, 78–88 and 8, respectively, are shown in this Figure).

FIG. 10 illustrates the results. As seen from FIG. 10, the amino acid added to Position +4 has little to do with the GalNAc acceptor activity and the effect of the side chain is even lower if compared with that of the side chain for Position -1 or +2. Thus, the amino acid at Position +4 is by no means significant nor essential. However, it may have a certain effect in some cases because it provides a slightly higher activity level for glycine, glutamine, glutamic acid, alanine, asparagine, aspartic acid, arginine, cysteine and isoleucine.

Example 11
Alteration of a Peptide to the Mucin Type Glycoprotein by Inserting Peptide Sequence Having GalNAc Acceptor Activity A peptide sequence having a GalNAc acceptor activity was introduced into a protein to confirm that a mucin type sugar chain can bind to it.

As a model protein, a derivative of glutathione S-transferase (GST) from *Schistosoma japanicum* was used. The derivative of GST (GST-3X) can easily be prepared on a mass production basis from *E. coli* with commercially available plasmid pGEX-3X (Pharmacia Biotech). The derivative of GST had a peptide sequence SDLIEGR-GIPGNSS added to the C-terminal of native GST. The gene of the protein contained in plasmid pGEX-3X was used.

Figure 11:
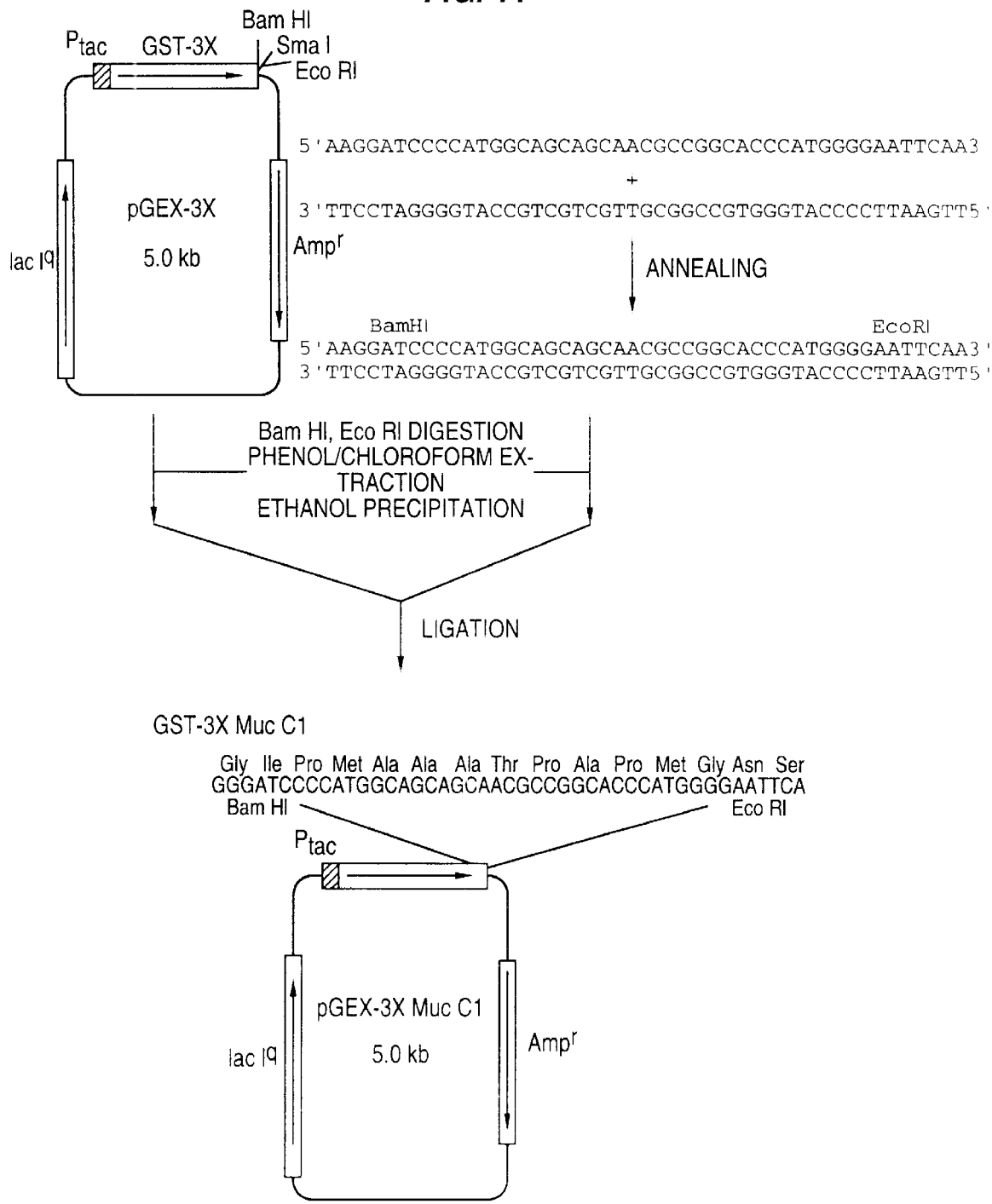
FIG. 11 illustrates a construction of expression plasmid pGEX-3X Muc C1 which is used for the production of protein GST-3X Muc C1 including a peptide sequence having GalNAc acceptor activity at the C-terminal region of protein GST (SEQ ID NOS:89–90, 116 and 115, respectively, are shown in this Figure).

A recombinated gene coding for a mutant protein in which a peptide sequence having a GalNAc acceptor activity was inserted in a downstream region of GST-3X was constructed. The construction of the gene is illustrated in FIG. 11. The procedures for gene manipulation were according to the methods described in Molecular Cloning [J. Sambrook et al., Cold Spring Harbor Laboratory Press (1989)], unless otherwise noted.

The sequence MAAATPAPM containing AAATPAP revealing the high level activity was used as a sequence having the GalNAc acceptor activity. The DNA coding for the peptide sequence MAAATPAPM was prepared in the following manner. The following two single-strand DNAs were prepared with 394DNA/RNA Synthesizer available from Applied Biosystems.

5'-AAGGATCCCCATGGCAGCAGCAACGCCGGCACC-CATGGGGAATTCAA-3'(Synthesized DNA 1 (SEQ ID NO:89))

5'-TTGAATTCCCCATGGGTGCCGGCGTTGCTGCTG-CCATGGGGATCCTT-3'(Synthesized DNA 2 (SEQ ID NO:90))

Subsequently, 50 µl of a solution containing 10 mM Tris-HCl (pH 8.0), 5 mM $MgCl_2$, 100 mM NaCl, 1 mM 2-mercaptoethanol and 1 nmol of each of the above synthesized DNAs were prepared. The solution was then warmed to 75° C. for 10 minutes and thereafter left to room temperature for annealing to produce a double-strand DNA, which was the desired DNA. A 5 µl portion of the solution thus obtained was taken and the double-strand DNA was cut with EcoR I and BamH I and inserted between the same restriction enzyme sites of pGEX-3X to construct plasmid pGEX-3X Muc C1 according to a conventional method. The plasmid contained a DNA encoding the mutant, GST-3X Muc C1, n which MAAATPAPM was inserted between the 228th proline and the 229th glycine of the GST-3X. The sequence of the inserted region was confirmed by 373 A DNA sequencer (Applied Biosystems) with 5'pGEX Sequencing Primer (Pharmacia Biotech) and PRISM, Dye Terminator Cycle Sequencing Kit (Applied Biosystems).

The mutant protein containing the peptide sequence of MAAATPAPM (SEQ ID NO:105) inserted in a C-terminal region of GST-3X was prepared by utilizing *E. coli* in the following manner. *E. coli* BL 21 (Pharmacia Biotech) was transformed with pGEX-3X Muc C1 by means of the $CaCl_2$ method and then precultured in 5 ml of 2×YTG culture medium (16 g/l Tryptone, 10 g/l Yeast extract, 5 g/l NaCl, pH 7.0) containing 100 µg/ml of ampicillin, which were precultured with shaking overnight at 37° C. Subsequently, it was moved to 500 ml of the similar culture medium and cultured with shaking for 2.5 hours at 37° C. (O.D.= 0.5–1.0). A portion of 100 mM of Isopropyl-β-D-thiogalactopyranoside (IPTG) was added to the culture solution to achieve a final concentration of 0.5 mM. The solution was then centrifuged at 5,000 rpm (4,470×g) for 10 minutes at 4° C. to collect cells, which were then washed with 50 ml of 20 mM Tris-HCl (pH 7.5) and 140 mM NaCl and subjected to another centrifugation under the same conditions for collection. The cells were resuspended in 50 ml of 20 mM Tris-HCl (pH 7.5) and 140 mM NaCl and lyzed with a ultrasonic processer. The product was centrifuged at 15,000 rpm (27,700×g) for 30 minutes at 4° C. and the supernatant was filtered by a membrane with a pore size of 0.22 µm and 10% Triton X-100 was added to achieve a final concentration of 0.1%. The obtained solution was used as a crude enzyme solution.

The crude enzyme solution was put on 1 ml of Glutathione Sepharose 4B column (Pharmacia Biotech) which was in advance equilibrated with 20 mM Tris-HCl (pH 7.5), 140 mM NaCl and 0.1% Triton X-100 and then washed with 20 mM Tris-HCl (pH 7.5), 140 mM NaCl and 0.1% Triton X-100. Subsequently, 1 ml of a solution containing 50 mM Tris-HCl (pH 8.0), 140 mM NaCl, 0.1% Triton X-100, 5 mM dithiothreitol and 10 mM glutathione (reduced form) was added to the column, which was settled for 10 minutes at room temperature and then eluted with 9 ml of the same buffer solution to obtain 1 ml-fractions. The quantification of the protein of the eluted fractions was performed with Protein Assay Kit (Japan Bio-Rad laboratory) and the GST activity was measured by GST Detection Module (Pharmacia Biotech). The gel electrophoresis (SDS-PAGE) of the protein was performed by a method proposed by U. K. Laemmli [Nature (London), Vol.227, pp.680–685 (1970)] using 13% gel as a separation gel. The GST-3X Muc C1 detected in the eluted fractions showed a GST activity equal to that of GST-3X and a single band with a molecular weight of about 28 K on SDS-PAGE.

A sample as control GST-3X was also prepared in a similar manner as above.

The GalNAc transfer to GST-3X and GST-3X Muc C1 was analyzed according to the method described for determining the GalNAc acceptor activity of peptide except that 5 nmol of the GST-3X mutant was used instead of 100 nmol peptide.

Figure 12:
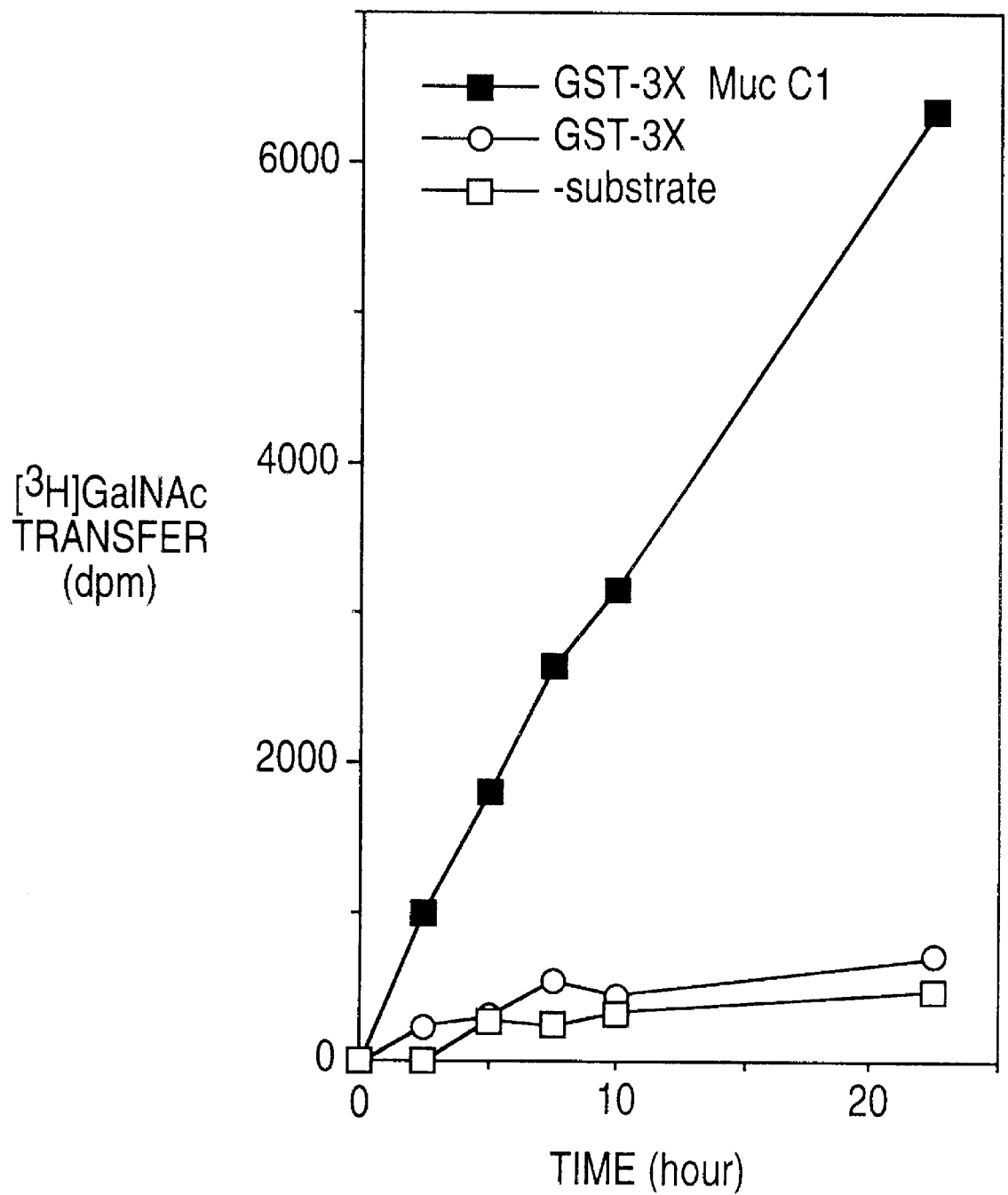
FIG. 12 is a graph showing the amount of GalNAc transferred to GST-3X Muc C1 including a peptide sequence having GalNAc acceptor activity at the C-terminal region of protein GST and controls of protein having no such peptide sequence.

FIG. 12 shows the results. As seen from FIG. 12, no substantial GalNAc transfer to GST-3X was observed, whereas GalNAc transfer to GST-3X Muc C1 increased as time went by. This fact shows that a protein can be altered to the mutant that can bind a mucin type sugar chain by inserting a peptide sequence having a GalNAc acceptor activity into the protein.

Example 12

Alteration of a Peptide to the Mucin Type Glycoprotein by Adding Peptide Sequence having GalNAc Acceptor Activity In this example, a model protein GST-3X was used same as in Example 11. However, in this example, a peptide sequence having a GalNAc acceptor activity was added to the N-terminal side of the protein to confirm that the protein can be altered to show an ability of binding a mucin type sugar chain.

Figure 13:
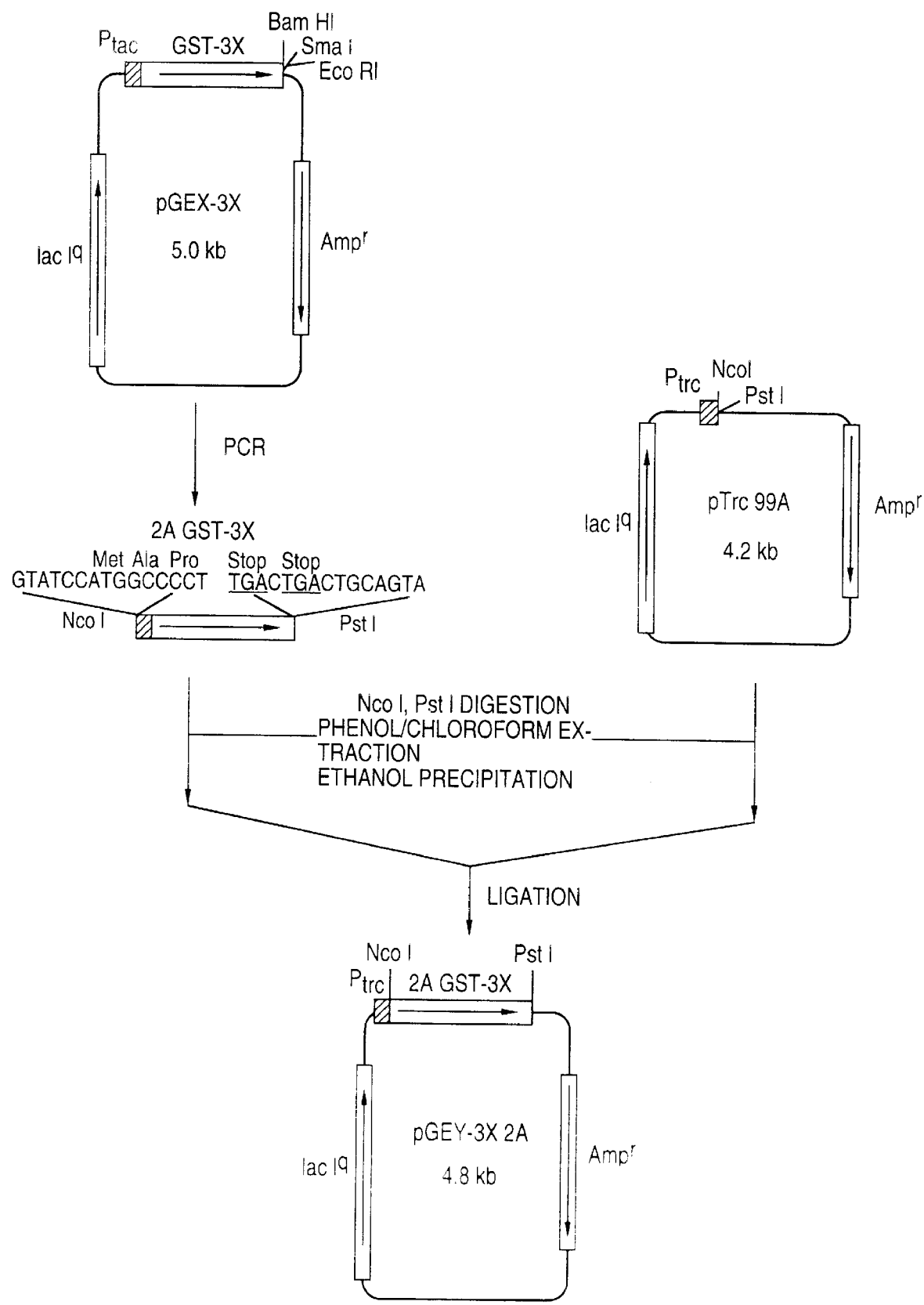
FIG. 13 illustrates a construction of expression plasmid pGEY-3X 2A Muc N1 which is used for the production of protein GST-3X 2A Muc N1 including a peptide sequence having GalNAc acceptor activity at the N-terminal side of protein GST. The illustration is complete with FIG. 14 (SEQ ID NOS:117 and 158, respectively, are shown in this Figure).
Figure 14:
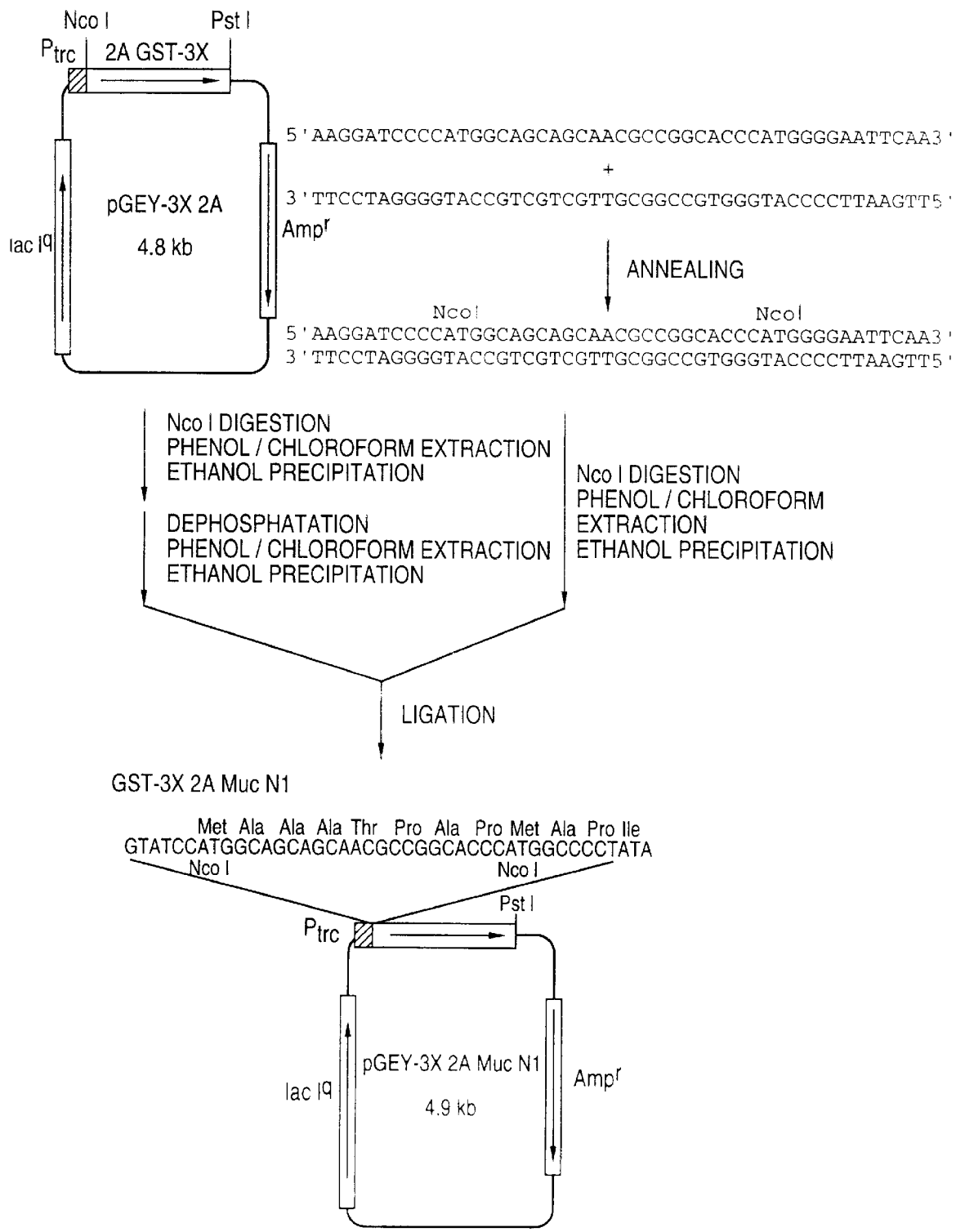
FIG. 14 illustrates a construction of expression plasmid pGEY-3X 2A Muc N1 which is used for the production of protein GST-3X 2A Muc N1 having a peptide sequence with GalNAc acceptor activity at the N-terminal side of protein GST (SEQ ID NOS:89–90, 119 and 118, respectively, are shown in this Figure).

The construction of a mutant gene was conducted according to the procedures illustrated in FIGS. 13 and 14.

The GST-3X gene in pGEX-3X does not have any restriction site in the N-terminal region for inserting a DNA fragment of a peptide sequence having a GalNAc acceptor activity. Therefore, a gene for GST-3X 2A having a restriction site of Nco I was prepared by polymerase chain reaction (PCR). At first, the following primers were synthesized with 394 DNA/RNA Synthesizer available from Applied Biosystems.

5'-GTATCCATGGCCCCTATACTAGGTTATTGG-3' (Synthesized DNA 3 (SEQ ID NO:91))
5'-TACTGCAGTCAGTCAGTCACGATGAATTCC-3' (Synthesized DNA 4 (SEQ ID NO:92))

The PCR reaction was conducted with a reaction solution containing 2.5 ng of template DNA, pGEX-3X, 0.5 µM of Synthesized DNA 3, 0.5 µM of Synthesized DNA 4, 8 µl of dNTP mixture (Takara Shuzo), 10 µl of 10×AmpliTaq DNA Polymerase Buffer (Takara Shuzo) and 2.5 unit of AmpliTaq DNA Polymerase (Perkin-Elmer), to which two drops of mineral oil (Takara Shuzo) was added, and DNA Thermal Cycler (tradename: Perkin-Elmer). The PCR process was conducted as 35 cycles of 1 minute at 94° C., 2 minutes at 55° C. and 2 minutes at 72° C., followed by a single step of 10 minutes at 72° C. and a temperature fall to 4° C. After the reaction, Pronase K (Boehringer Mannheim), ethylenediaminetetraacetic acid disodium salt (EDTA) and sodium dodecyl sulfate (SDS) were added respectively to 12 mg/ml, 10 mM and 0.8%. The mixture was warmed to 37° C. for 30 minutes and then to 65° C. for 10 minutes. Thereafter, the PCR reaction product was extracted by phenol, purified by ethanol precipitation and cut by restriction enzymes Nco I and Pst I to produce the desired DNA. The DNA was then inserted between the same restriction sites of pSL1190 (Pharmacia Biotech) according to a conventional method. The sequence of the inserted DNA was analyzed by 373A DNA Sequencer of Applied Biosystems with PRISM, Dye Primer Cycle Sequencing Kit (Applied Biosystems). The obtained DNA of GST-3X 2A was characterized in that the second amino acid, serine, from the N-terminal of GST-3X was changed to alanine by introducing Nco I site.

Then, the GST-3X 2A DNA was cut from pSL1190 by Nco I and Pst I, and inserted between the same restriction sites of pTrc99A (Pharmacia Biotech) to obtain pGEY-3X 2A. The plasmid pGEY-3X 2A is very similar to pGEX-3X except that it contains GST-3X 2A gene having an Nco I site at the N-terminal where a DNA can be inserted and that the promoter is switched from tac to trc.

Finally, a plasmid of pGEY-3X 2A Muc N1 containing GST-3X 2A Muc C1 gene having a peptide sequence of MAAATPAP (SEQ ID NO:104) at the N-terminal was prepared in a manner as described below. A gene coding for the peptide sequence MAAATPAP (SEQ ID NO:104) was prepared by synthesizing single-strand Synthesized DNA 1 and Synthesized DNA 2 same as those of Example 11 and annealing them in 50 µl of a solution containing 50 mM Tris-HCl (pH 7.5), 10 mM MgCl₂, 100 mM NaCl and 1 mM 2-mercaptoethanol. In 5 µl of the solution thus obtained, the double-strand DNA was cut by Nco I and inserted into the Nco I site of pGEY-3X 2A to produce plasmid pGEY-3X 2A Muc N1. The plasmid has MAAATPAP (SEQ ID NO:106) upstream to the methionine at the N-terminal of GST-3X and contains a DNA coding for a mutant, GST-3X 2A Muc N1, in which the serine at the second position of GST-3X had been changed to alanine. The sequence of the inserted region was confirmed by 373A DNA Sequencer (Applied Biosystems) with 5'-GTTGACAATTAATCATCCGGCTCGT-3' ((SEQ ID NO:106) synthesized and purified with HPLC by Kurasiki-Bouseki) and PRISM, Dye Terminator Cycle Sequencing Kit (Applied Biosystems).

The mutant protein GST-3X 2A Muc N1 was prepared by utilizing E. coli and analyzed as in the case of GST-3X Muc C1 described in Example 11. The GST-3X 2A Muc N1 which was detected in an eluted fraction from Glutathione Sepharose 4B column showed a GST activity equivalent to that of GST-3X. Further, it was detected as a single band with a molecular weight of about 28 K by SDS-PAGE.

The transfer of GalNAc to GST-3X 2A Muc N1 and to GST-3X was analyzed in the same manner as the method for measuring the GalNAc acceptor activity except that 5 nmol GST mutant was used instead of 100 nmol peptide.

Figure 15:
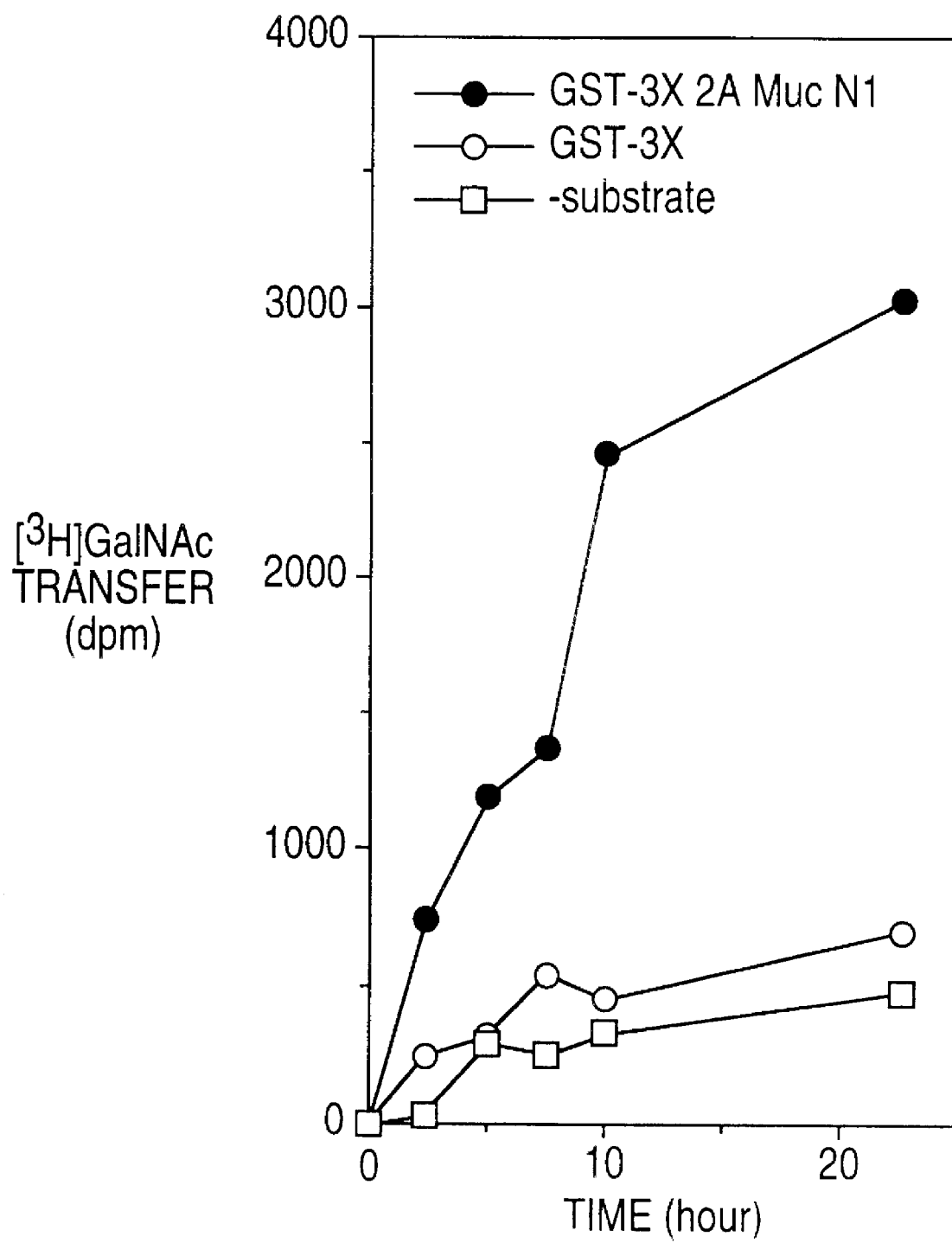
FIG. 15 is a graph showing the amount of GalNAc transferred to GST-3X 2A Muc N1 including a peptide sequence having GalNAc acceptor activity at the N-terminal side of protein GST and controls of protein having no such peptide sequence.

FIG. 15 shows the results. As seen from FIG. 15, no substantial GalNAc transfer to GST-3X was observed, whereas GalNAc transfer to GST-3X Muc C1 increased as time went by. This suggests that a protein can be altered to the protein that can bind a mucin type sugar chain by adding a peptide sequence having a GalNAc acceptor activity into the protein.

The above results and the results of Example 11 show that, when introducing a peptide sequence having a GalNAc acceptor activity into a protein, the position for introducing the peptide sequence in the protein is not particularly limited.

Example 13

Introduction of Various Peptide Sequences Having GalNAc Acceptor Activity into a Protein to Alter the Mucin Type Sugar Glycoprotein The transfer of GalNAc to GST-3X Muc C1 in Example 11 and that of GalNAc to GST-3X 2A Muc N1 in Example 12 were confirmed by a method in which SDS-PAGE and fluorography are combined.

In addition, GST-3X Muc C2, GST-3X Muc C3 and GST-3X Muc C4 were prepared by using a model protein of GST-3X as in the case of Example 11 but introducing respective peptide sequences that show a GalNAc acceptor activity and are different from that of GST-3X Muc C1 into the C-terminal side. For these mutants, GalNAc transfer activities were examined as in the case of the preceding two examples.

Figure 16:
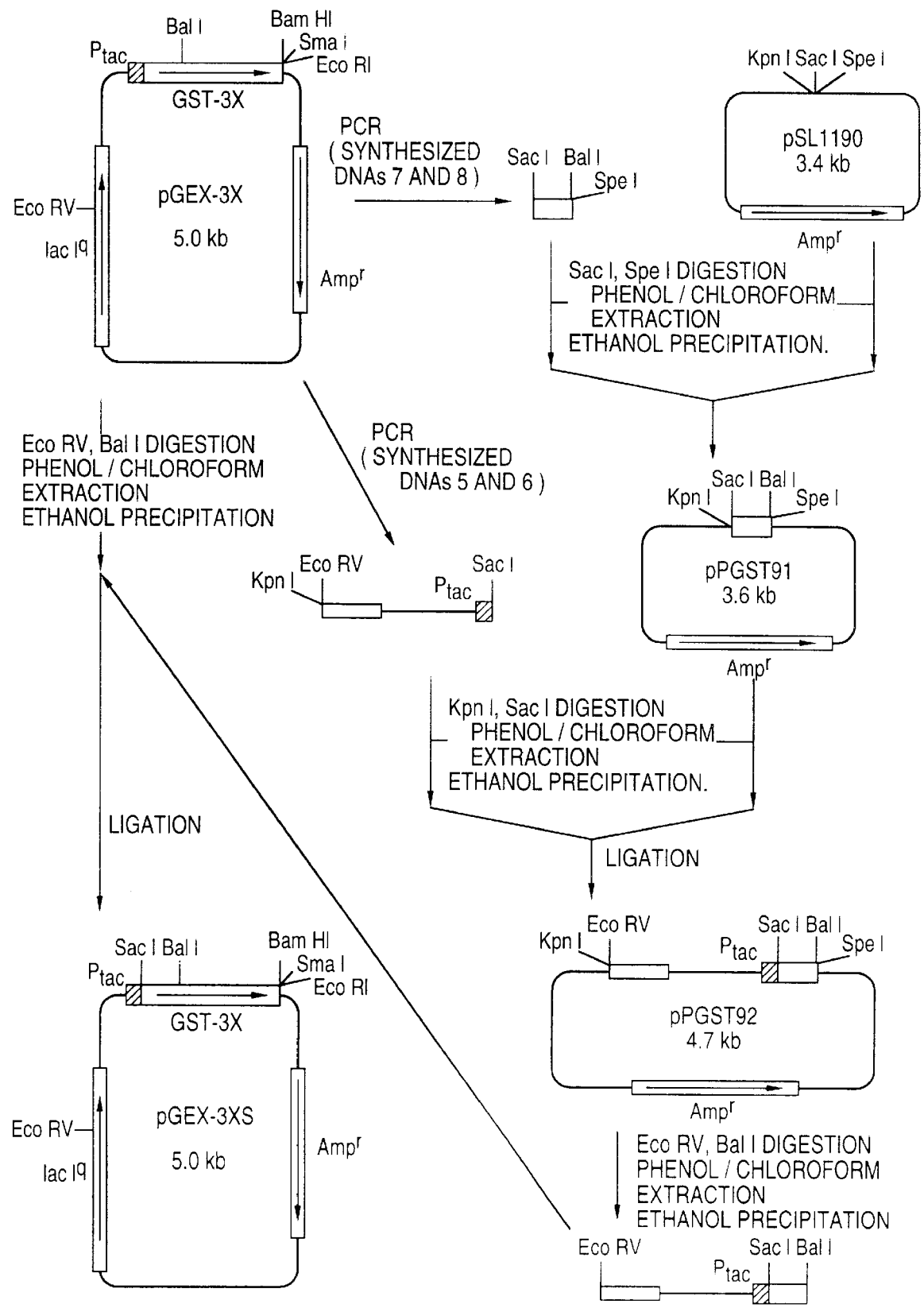
FIG. 16 illustrates a construction of expression plasmid pGEX-3XS which is used for the production of a GST mutant including a peptide sequence having GalNAc acceptor activity at the C-terminal side of protein GST.

The restriction sites in plasmid pGEX-3X have limitations for modifying the peptide sequence in the C-terminal region of the model protein. Therefore, plasmid pGEX-3XS was prepared with PCR for preparing various mutant forms of the model protein. The plasmid was constructed in a manner as illustrated in FIG. 16.

The following primer DNAs were synthesized with 394DNA/RNA Synthesizer available from Applied Biosystems.

5'-ATGGTACCATGCGCGCCATTACCGAGT-3' (Synthesized DNA 5 (SEQ ID NO:93))
5'-CCGAGCTCTGTTTCCTGTGTGAAATTGT-3' (Synthesized DNA 6 (SEQ ID NO:94))
5'-CAGAGCTCATGTCCCCTATACTAGGTTA-3' (Synthesized DNA 7 (SEQ ID NO:95))
5'-GGACTAGTCATGTTGTGCTTGTCAGCTA-3' (Synthesized DNA 8 (SEQ ID NO:96))

The PCR process was conducted as described in Example 12 with pGEX-3X as a template DNA and the Synthesized DNAs 5 and 6 or Synthesized DNAs 7 and 8 in combination, provided that 10×AmpliTaq DNA Polymerase Buffer and AmpliTaq DNA Polymerase were replaced respectively by PCR buffer, 10×conc. with MgSO$_4$ (Boehringer Mannheim) and Pwo DNA polymerase (Boehringer Mannheim). The reaction product by utilizing the combination of Synthesized DNAs 7 and 8 was applied to agarose gel electrophoresis to collect about a 0.2kb of DNA fragments, which were then extracted with phenol and purified by ethanol precipitation. The DNA fragments were cut by restriction enzymes Sac I and Sph I and inserted between the same restriction enzyme sites of pSL1190 (Pharmacia Biotech) according to a conventional method to produce pPGST91. The sequence of the inserted DNA was analyzed by 373A DNA Sequencer of Applied Biosystems with PRISM, Dye Primer Cycle Sequencing Kit (Applied Biosystems). The reaction product by utilizing the combination of Synthesized DNAs 5 and 6 was subjected to a similar process and about a 1.2 kb DNA fragment was isolated and purified, followed by cutting with restriction enzymes Sac I and Kpn I. The fragments were inserted between the same restriction enzyme sites of pPGST91 according to a conventional method to produce pPGST92. Then, pPGST92 was cut with restriction enzymes EcoR V and Bal I. The obtained 1.3 kb of fragments was inserted between the same restriction enzyme sites of pGEX-3X according to a conventional method to construct pGEX-3XS.

FIGS. 17A, 17B and 17C respectively shows restriction enzyme maps of plasmids pGEX-3XS Muc C2, pGEX-3XS Muc C3 and pGEX-3XS Muc C4 which are used for expressing GST-3X Muc C2, GST-3X Muc C3 and GST-3X Muc C4.

These plasmids were constructed in a manner as described below.

The following primer DNAs were synthesized.
5'-CGTCTAGACCGTCAGTCAGTCACGATGAAGGCG-CGGGGGTCCCAC-3' (Synthesized DNA 9 (SEQ ID NO:97))
5'-CGTCTAGACCGTCAGTCAGTCACTATTAAGGCGC-GGGGGTCCCAC-3' (Synthesized DNA 10 (SEQ ID NO:98))
5'-CGTCTAGACCGTCAGTCAGTCACGATGAAGGCC-CGGGGGTCCCAC-3' (Synthesized DNA 11 (SEQ ID NO:99))

The PCR process was conducted as described above with pGEX-3X as a template DNA and the Synthesized DNAs 7 and 9, Synthesized DNAs 7 and 10 and Synthesized DNAs 7 and 11 in combination. After the reaction, each of the PCR reaction products was purified as in the case of Example 12, cut with restriction enzymes Sac I and Xba I and inserted between the same restriction sites of pBluescript II KS+ (Stratagene). The constructed plasmids were respectively named as pBGSTC2 for the combination of Synthesized DNAs 7 and 9, pBGSTC3 for the combination of Synthesized DNAs 7 and 10 and pBGSTC4 for the combination of Synthesized DNAs 7 and 11. The sequence of each of the inserted DNAs was confirmed by 373A DNA Sequencer of Applied Biosystems with PRISM, Dye Primer Cycle Sequencing Kit (–21 M13) and (M13 Rev.) (Applied Biosystems). Finally, each of pBGSTC2, pBGSTC3 and pBGSTC4 was cut with restriction enzymes Sac I and EcoR I to obtain about 0.7kb of fragments. Each of the fragments was inserted between the same restriction enzyme sites of pGEX-3XS to provide pGEX-3XS Muc C2, pGEX-3XS Muc C3 or pGEX-3XS Muc C4.

The mutant proteins GST-3X Muc C2, GST-3X Muc C3 and GST-3X Muc C4 were prepared by utilizing *E. coli* and analyzed in a manner as described for GST-3X Muc C1 in Example 11. Each of GST-3X Muc C2, GST-3X Muc C3 and GST-3X Muc C4 detected in eluted fractions from Glutathione Sepharose 4B column showed a specific GST activity comparable to that of GST-3X. Further, they were detected as a single band with a molecular weight of about 27 K by SDS-PAGE.

The transfer of GalNAc to each of the mutant GSTs was analyzed in the following manner, where SDS-PAGE and fluorography was combined. A 50 μl of a solution (50 mM Imidazole-HCl (pH 7.2), 10 mM MnCl$_2$, 0.5% Triton X-100 and 150 μM UDP-[$^3$H]GalNAc) containing 5 nmol of the GST-3X mutant and 50 mU of partially purified 0-GalNAc T derived from colostrum of cow was prepared and kept at 28° C. for 20 hours. Then, 50 μl of 2×SDS/sample buffer (125 mM Tris-Hcl (pH 6.8), 4% SDS, 4% 2-mercaptoethanol, 20% glycerol and 0.004% Bromophenol Blue) was added thereto and left in a boiling water for 5 minutes. Thereafter, 30 μl of the reaction solution was applied to 12.5% SDS-PAGE. The gel was then immersed in a fixative solution (2-propanol/water/acetic acid (25:65:10)) for 30 minutes and then in Amprify (Amersham) for 30 min. Then, the gel was vacuum dried at 80° C. and in close contacted with an X-ray film at –80° C. for 15 days for exposure.

Figure 18:
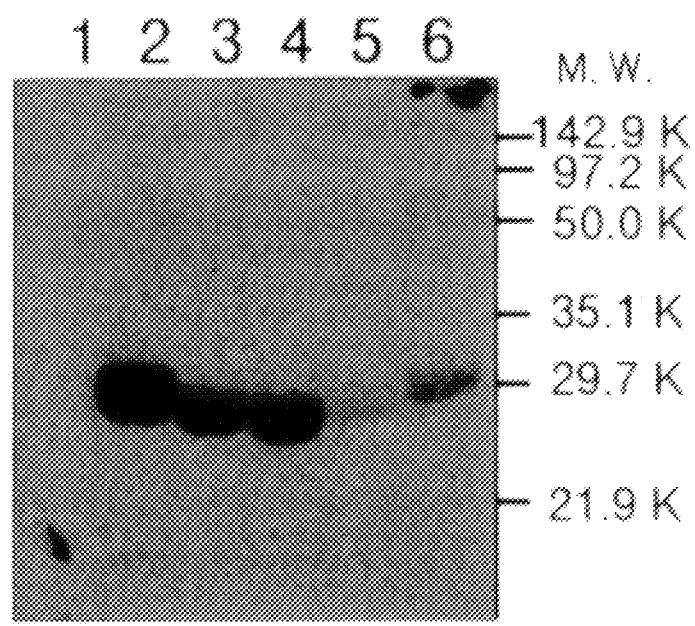
FIG. 18 is a graph showing the amount of GalNAc transferred to proteins GST-3X, GST-3X Muc C1, GST-3X Muc C2, GST-3X Muc C3, GST-3X Muc C4 and GST-3X 2A Muc N1.

FIG. 18 shows the results. While no GalNAc transfer to GST-3X was observed, GalNAc was clearly transferred to GST-3X Muc C1, GST-3X Muc C2, GST-3X Muc C3, GST-3X Muc C4 and GST-3X 2A Muc N1. This indicates that the sequences represented by the formula: X(-1)-T-P-X(-2)-P wherein X(-1) and X(-2) represent any amino acid functions in a protein have a mucin type sugar chain. It was also found that, for introducing a peptide sequence, there are no limitations on the region. In addition, there are no limitations on the type of the introduction of the peptide sequence, i.e., insertion, addition and substitution can be appropriately used for introducing the peptide sequence. As clearly seen from the case of GST-3X Muc C2 and GST-3X Muc C4, a protein capable of accepting a mucin type sugar chain can be easily obtained by replacing only two or three amino acid residues. This suggests that this technique is fairly useful for modifying a protein to be glycosylated with mucin type sugar chain.

Example 14
Introduction of a Peptide Sequence Having GalNAc Acceptor Activity into a Protein and Secretory Expression of a Mutant Protein Having a Mucin Type Sugar Chain in Eucaryotic Cells Examples 11 to 13 proved that proteins can be altered to the substrate proteins for in vitro GalNAc transfer by introducing appropriate peptide sequences having a GalNAc acceptor activity. Since *E. coli* are devoid of a biosynthetic pathway of mucin type sugar chains, GalNAc should be transferred in vitro to recombinant proteins produced in *E.* coli. To the contrary, since eucaryotic cells have such a pathway, they may be utilized for directly producing mucin type glycoproteins. Therefore, in this example, a gene encoding a mutant protein including a peptide sequence having a GalNAc acceptor activity was prepared and secretory expressed in COS7 cells to confirm that the mutant mucin type glycoprotein can be produced.

As in the preceding examples, GST was used as a model protein. GST-3X Muc C1 that had been proved to be transferred GalNAc and GST-3X being no transferred GalNAc in Example 11 and 13 were expressed in COS7 cells.

Since GST is an intracellular protein, genes of GST-3X and GST-3X Muc C1 to which a signal sequence for secretion was added to the N-terminal were prepared by a 2-step PCR process. The signal sequence of human erythropoietin (hEPO) [K. Jacobs et al., Nature, Vol.313, pp.806–810 (1985)] was used in a manner as described below.

The following four different primer DNAs were prepared with 394DNA/RNA Synthesizer of Applied Biosystems.
5'-AACTCGAGAATTCATGGGGGTGCACGAATG-3' (Synthesized DNA 12 (SEQ ID NO:100))
5'-CAATAACCTAGTATAGGGGAGCCCAGGACTGGG-AGGCCCA-3' (Synthesized DNA 13 (SEQ ID NO:101))
5'-TGGGCCTCCCAGTCCTGGGCTCCCCTATACTAGG-TTATTG-3' (Synthesized DNA 14 (SEQ ID NO:102))
5'-CCTCTAGATCGTCAGTCACGTCAGATGAAT-3' (Synthesized DNA 15 (SEQ ID NO:103))

In the first step of the PCR process, a plasmid containing cDNA of hEPO as a template DNA [H. Ohashi et al., Biosci. Biotech. Vol.58, pp.758–759 (1994)] was used along with primers of Synthesized DNAs 12 and 13. The PCR reaction as described in Example 13 was carried out except annealing temperature was changed to 58° C. A similar PCR reaction was also carried out with pGEX-3X as a template DNA and Synthesized DNAs 14 and 15 as primers. Each of the reaction products was extracted once with chloroform and precipitated with ethanol twice, followed by dissolving in 50 μl of TE buffer. Template DNAs were prepared by mixing 1 μl of the signal peptide region and 1 μl of the PCR reaction product of GST. The second step of the PCR process was carried out with the prepared template DNA along with the Synthesized DNAs 12 and 15 as primers. The reaction and the purification of the reaction product were exactly the same as those in Example 13. After the product was cut with restriction enzymes Xho I and Xba I, the fragment thus obtained was inserted between the same restriction sites of pBluescript II KS+ according to a conventional method. The obtained plasmid was called pBEGST-3X. The sequence of the inserted region of the plasmid was confirmed with PRISM, Dye Primer Cycle Sequencing Kit (−21 M31) and (M13 Rev.) (Applied Biosystems) in the same manner as described in Example 13.

A gene of a secretion form protein of GST-3X Muc C1 was prepared in the same manner as described above except that pGEX-3X Muc C1 was used instead of pGEX-3X. pBEGST-3X Muc C1 was thus obtained.

Figure 19B:
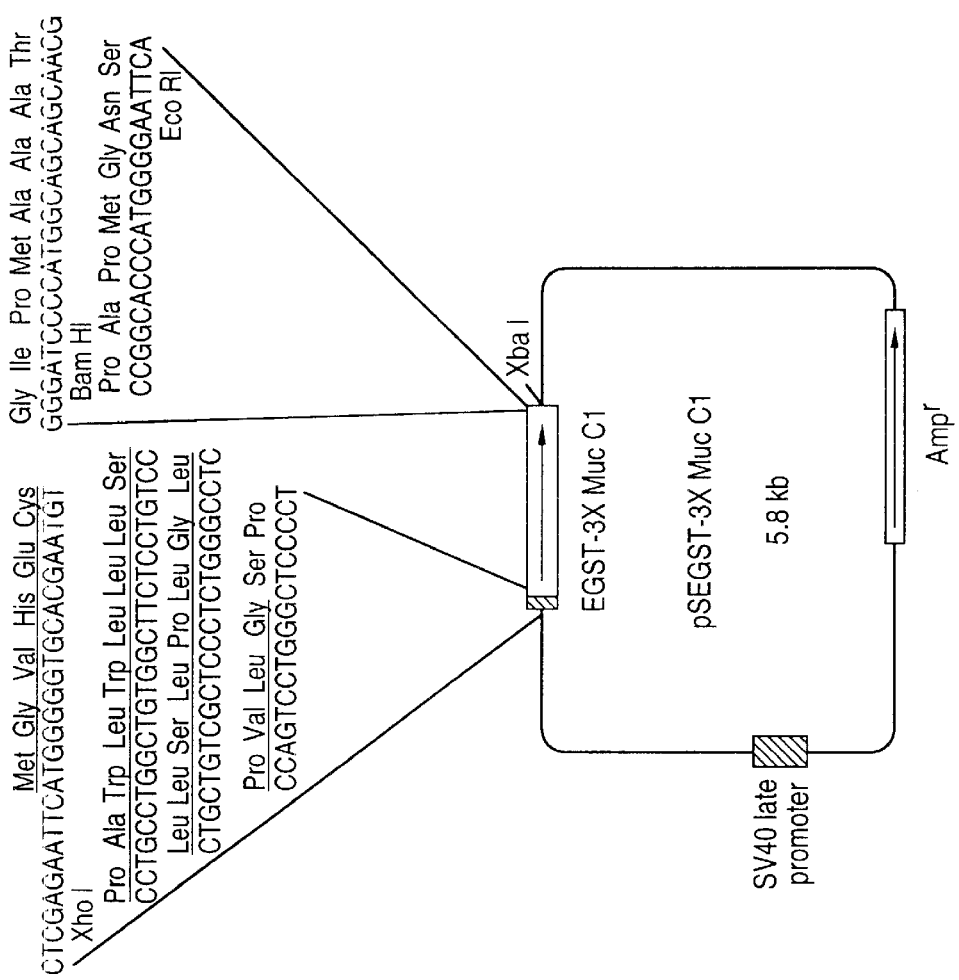
FIGS. 19A and 19B illustrate the structures of plasmids pSEGST-3X and pSEGST-3X Muc C1 for the secretory expression of EGST-3X and EGST-3X Muc C1 in COS7 cells (SEQ ID NOS:127, 126, 129, 128, 131, 130, 133, 132, 135, 134, 137 and 136, respectively, are shown in this Figure).
Figure 19A:
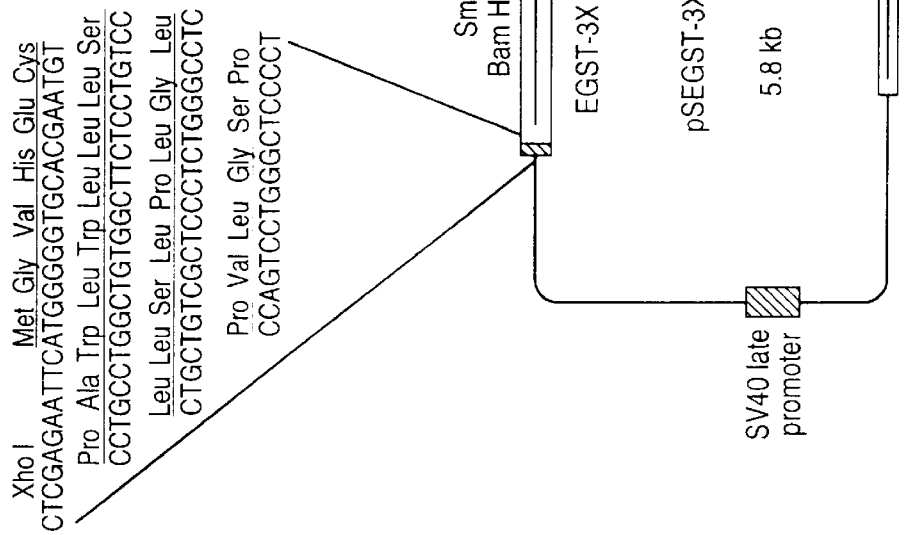

The insertion regions from pBEGST-3X and pBEGST-3X Muc C1 were cut out with restriction enzymes Xho I and Xba I and collected. Thereafter, they were inserted between the same restriction sites of plasmid vector pSVL for mammalian cells (Pharmacia Biotech) according to a conventional method to give pSEGST-3X and pSEGST-3X Muc C1. FIGS. 19A and 19B show restriction maps of the plasmids. It may be expected that, when the plasmids are introduced into a mammalian cell, EGST-3X and EGST-3X Muc C1 as the GST mutants which starts from the second serine from the N-terminal of the native GST-3X will be secreted into the culture.

Each of pSEGST-3X and pSEGST-3X Muc C1 was introduced into COS7 cells (Riken Cell Bank) by electroporation. More specifically, 10 μg of the plasmid was added to about 5×10⁶ cells in 0.8 ml of PBS(-) (Nissui Pharmaceutical) and the DNA was introduced with Gene Pulser (Japan Biolaboratory) at room temperature under the conditions of 1600 V and 25 μF. The cells were put on a 90 mm laboratory dish and cultured in Dulbecco's modified Eagle's medium containing 10 ml of 10% fetal bovine serum (Base Catalogue No. 12,430) (Gibco BRL) at 37° C. for 24 hours and thereafter moved to 10 ml of Dulbecco's modified Eagle's medium (Base Catalogue No. 26,063) (Gibco BRL) at 37° C. for 3 days.

The secreted GST mutant in the culture supernatant was purified with ½-scaled method, which was described in Example 11, concerning the E. coli culture with 0.5 ml of Glutathione Sepharose 4B column. The eluted fraction was condensed and changed to 10 mM potassium phosphate buffer (pH 6.2) with a Centricon-10 (Grace Japan).

The EGST-3X and EGST-3X Muc C1 thus obtained showed a specific GST activity comparable to that of GST-3X produced in E. coli. They were then subjected to an analysis including a treatment with glycosidases and a lectin blotting analysis in the following manner.

In the treatment with glycosidases, neuraminidase derived from *Arthrobacter ureafaciens* (Boehringer Mannheim) and O-glycanase (Genzyme) derived from *Diplococcus pneumoniae* were used. The treatment with neuraminidase was conducted by adding 40 mU of the enzyme to about 300 ng of the GST mutant in 40 μl of 20 mM potassium phosphate buffer (pH 6.2), followed by incubating the solution at 37° C. for 13 hours. In the treatment of neuraminidase and O-glycanase, the reaction solution of neuraminidase described above was heated to 37° C. for 1 hour, and then a 2mU of O-glycanase was added thereto before it was left for the reaction for 12 hours. As controls, a sample kept to 37° C. for 13 hours and an untreated sample were prepared. Each of the samples was reacted with SDS by adding a same amount of 2×SDS/sample buffer and a 15 μl of the reaction product was applied to SDS-PAGE. After electrophoresis, the gel was stained with 2D-silver staining reagent II "Daiichi" (Daiichi Pharmaceutical) to detect the protein band.

The lectin blotting analysis was carried out with DIG Glycan Differentiation Kit (Boehringer Mannheim). In this analysis, the procedure down to the SDS-PAGE analysis was the same that of the glycosidase treatment. Thereafter, the proteins were blotted on a PVDF membrane [M. Ogasawara et al., Protein Experiment Methods for the Study of Molecular Biology, Youdosha, 1994] and the structure of galactose (β1-3)N-acetylgalacosamine (Gal β1-3 GalNAc) was analyzed with DIG labelled lectin PNA.

Figure 20:
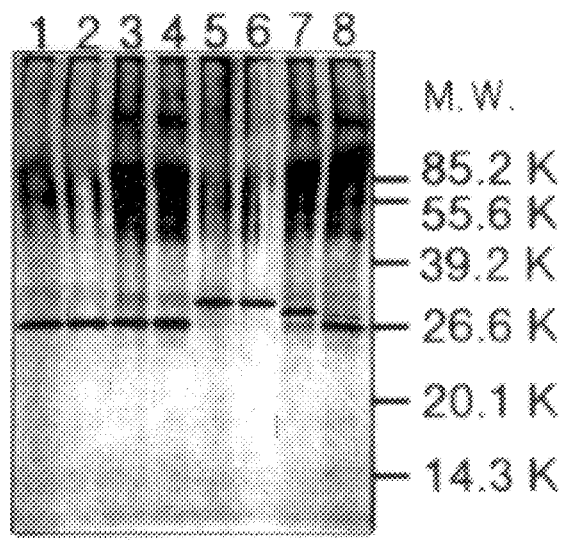
FIG. 20 is a gel showing the result of an analysis of glycosidase treatments of proteins EGST-3X and EGST-3X Muc C1 obtained by secretory expression in COS7 cells.

The results of the glycosidase treatment are shown in FIG. 20. The obtained EGST-3X was detected as a substantially single band with a molecular weight of about 27 K, which did not change after any glycosidase treatment. On the other hand, EGST-3X Muc C1 was detected as a single band that was shifted to the high molecular weight direction from the anticipated molecular weight of 28 K for the protein portion thereof. And, this band shifted to the low molecular weight direction by treating with neuraminidase or a combination of neuraminidase and O-glycanase. These facts show that a typical mucin type sugar chain is bound to EGST-3X Muc C1 and that the structure is Gal β1-3GalNAc with sialic acids.

Figure 21:
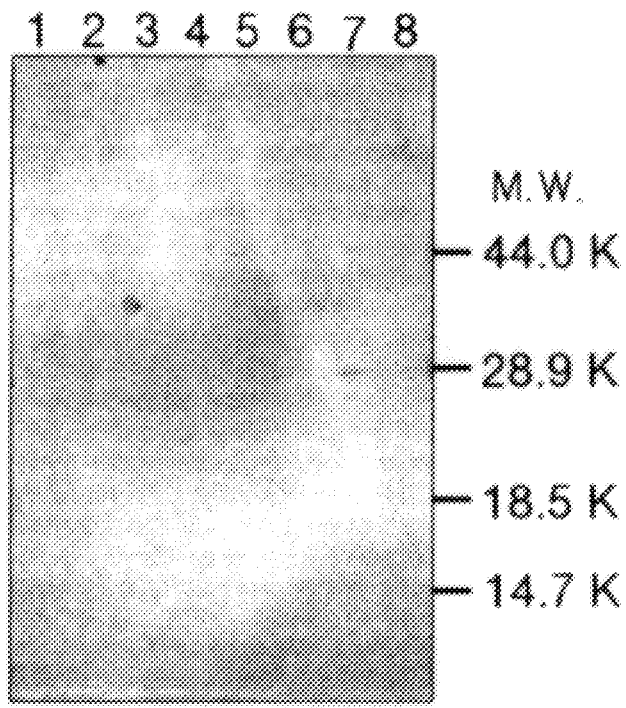
FIG. 21 is a gel showing the result of a lectin blotting analysis of proteins EGST-3X and EGST-3X Muc C1 obtained by secretory expression in COS7 cells.

FIG. 21 shows the results of the lectin blotting analysis. No band reacting with lectin PNA was detected as to EGST-3X regardless of the treatment with glycosidase. However, the band at about 28 K of EGST-3X Muc C1 treated with neuraminidase reacted with the lectin. Further, the band disappeared in a sample treated with neuraminidase and O-glycanase. Therefore, it is clear that the protein portion of EGST-3X Muc C1 has Gal β1-3GalNAc with sialic acids which is a typical mucin type sugar chain.

From the above findings, protein can be modified to glycoprotein having typical mucin type sugar chains comprising three or more different types of monosaccharides by introducing a peptide sequence having a GalNAc acceptor activity and secretory expressing the protein in eucaryotic cells.

Example 15
Introduction of Peptide Sequences Having a GalNAc Acceptor Activity into a Protein and secretory Expression of the Modified Protein Having a Mucin Type Sugar Chain in Eucaryotic Cells Example 14 showed that a GST mutant obtained by inserting a peptide sequence of MAAATPAPM (SEQ ID NO:105) was secretory expressed in COS7 cells and the produced EGST-3X Muc C1 had a typical mucin type sugar chain. Thus, in this example, each of GST-3X Muc C2, GST-3X Muc C3 and GST-3X Muc C4, that was confirmed to function, like GST-3X Muc C1, as a substrate for in vitro GalNAc transfer in Example 13, was fused with a signal peptide and secretory expressed in COS7 cells to confirm if the expressed proteins EGST-3X Muc C2, EGST-3X Muc C3 and EGST-3X Muc C4 can bind mucin type sugar chains. In addition, EGST-3X Muc C5 having a sequence of GTPGNSS, where amino acid at Position +1 is proline in the C-terminal region of EGST-3X, was also prepared.

Figure 22:
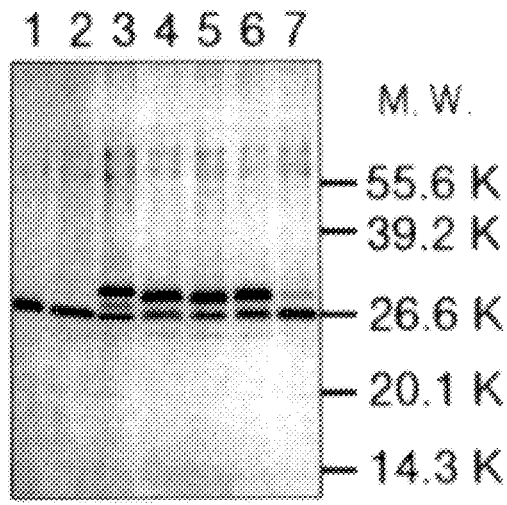
FIG. 22 is a gel showing the result of an SDS-PAGE analysis of proteins EGST-3X, EGST-3X Muc C1, EGST-3X Muc C2, EGST-3X Muc C3, EGST-3X Muc C4, and EGST-3X Muc C5 obtained by secretory expression in COS7 cells.

For the secretory expression of EGST-3X, EGST-3X Muc C1, EGST-3X Muc C2, EGST-3X Muc C3, EGST-3X Muc C4 and EGST-3X Muc C5, plasmids of pEEGST-3X, pEEGST-3X Muc C1, pEEGST-3X Muc C2, pEEGST-3X Muc C3, pEEGST-3X Muc C4 and pEEGST-3X Muc C5 were prepared as described below. FIG. 22 illustrates their restriction maps and the amino acid sequence in the mutated region.

After cutting pBEGST-3X with restriction enzyme Xba I, it was partially digested by restriction enzyme EcoR I to produce an about 0.9 kb DNA fragment containing a structural gene with a complete length of EGST-3X. The fragment was then inserted between EcoR I and Xba I sites of pEF18S [T. Kato et al., J. Biochem, Vol.118, pp.229–236 (1995) and S. Mizushima et al., Nucleic Acid Res. Vol. 18, 5322(1990)] according to a conventional method to produce pEEGST-3X. pEF18S was used in expectation of a high level of expression, because the level of the expression of the GST mutant in the plasmid vector pSVL was not so high in Example 14.

pEEGST-3X Muc C1 was constructed in the same manner as described above by using pBEGST-3X Muc C1 in place of pBEGST-3X.

pEEGST-3X Muc C2 was constructed by cutting pBGST C2 of Example 13 with restriction enzymes Bal I and Xba I to produce about an 0.5 kb DNA fragment and replacing the region having the same restriction sites of pEEGST-3X with the fragment. pEEGST-3X MucC3 and pEEGST-3X MucC4 were also constructed from pBGST C3 and pBGST C4 of Example 13, respectively.

pEEGST-3X Muc C5 was constructed in a manner as described below. The following primer DNA was synthesized.

5'-CGTCTAGACCGTCAGTCAGTCACGATGAATTGC-CGGGGGTCCCAC-3' (Synthesized DNA 16 (SEQ ID NO:107))

The PCR process as described in Example 13 was conducted except that pGEX-3X was used as a template DNA and Synthesized DNA 7 of Example 13 was combined with Synthesized DNA 16 as primers. After the reaction, the PCR product was purified by the method described in Example 12 and cut with restriction enzymes SacI and Xab I. The fragment was inserted between the same restriction sites of pBluescript II KS+(Stratagene). The plasmid thus obtained was called pBGSTC5. The sequence of the inserted fragment was confirmed by 373A DNA Sequencer available from Applied Biosystems with PRISM, Dye Primer Cycle Sequencing Kit (-21M13) and (M13Rev.) (Applied Biosystems). About a 0.5 kb DNA fragment was obtained by cutting pBGSTC5 with restriction enzymes Bal I and Xba I and substituted with the region having the same restriction enzyme sites of pEEGST-3X to construct pEEGST-3X Muc C5.

Each of the prepared plasmids of pEEGST-3X, pEEGST-3X Muc C1, pEEGST-3X Muc C2, pEEGST-3X Muc C3, pEEGST-3X Muc C4 and pEEGST-3X Muc C5 was introduced into COS7 cells and the GST mutant that was secreted from the cells into the culture was purified and condensed in a manner as described in Example 14. The obtained EEGST-3X, EEGST-3X Muc C1, EGST-3X Muc C2, EGST-3X Muc C3, EGST-3X Muc C4 and EGST-3X Muc C5 showed a specific activity level comparable to that of GST-3X produced by E. coli. A Part of each sample was analyzed by 13% SDS-PAGE and silver staining to detect protein bands.

Figure 23:
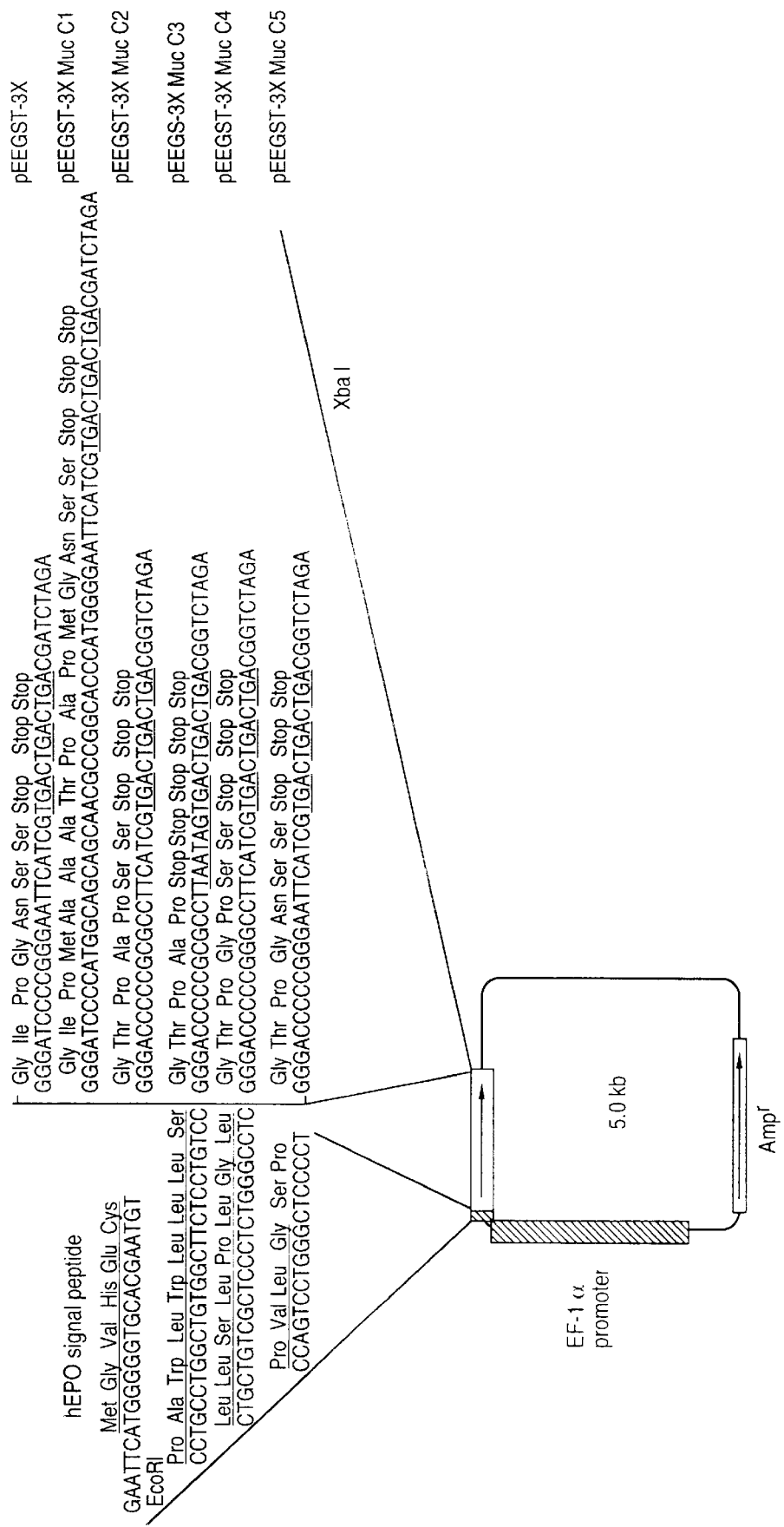
FIG. 23 illustrates the structures of plasmids pEEGST-3X, pEEGST-3X Muc C1, pEEGST-3X Muc C2 and pEEGST-3X Muc C3, pEEGST-3X Muc C4 and pEEGST-3X Muc C5 for the production of proteins EGST-3X, EGST-3X Muc C1, EGST-3X Muc C2, EGST-3X Muc C3, EGST-3X Muc C4 and EGST-3X Muc C5, respectively (SEQ ID NOS:139, 138, 141, 140, 143, 142, 145, 144, 147, 146, 149, 148, 151, 150, 153, 152, 155, 154, 157, and 156, respectively, are shown in this Figure).

FIG. 23 shows the results. EGST-3X which was proved to have no sugar chain in Example 14 showed a single band at about 27 K. In the case of EGST-3X Muc C1, on the other hand, the major signal was found at the positions proved to be binding a mucin type sugar chain in Example 14 and the minor signal was found at about 28 k which is corresponding to the protein without sugar chains. Similarly, all of EEGST-3X Muc C2, pEEGST-3X Muc C3 and pEEGST-3X Muc C4 gave bands corresponding to proteins having a mucin type sugar chain similar to the case of EGST-3X Muc C1. To the contrary, EGST-3X Muc C5 gave the major band corresponding to protein without sugar chains and the minor band corresponding to protein having a mucin type sugar chain.

The above results proved that a protein can be modified into a typical glycoprotein having a mucin type sugar chain by introducing any of various peptide sequences having a GalNAc acceptor activity into the protein and expressing the protein in an eucaryotic cell. More specifically, the results make it clear that various peptide sequences having a GalNAc acceptor activity described in Examples 1 to 10 can also function in a protein as the acceptor very well through in vivo biosynthesis pathway of mucin type sugar chains in eucaryotic cells. In addition, the results of the introduction of peptide sequences prove that this technique is fairly useful because the modificaiton of a mucin sugar chain needs the alteration of only one to three amino acid residues including sugar chain binding site in a protein. Furthermore, the comparison of EGST-3X Muc C5 having a proline only at Position +1 and EGST-3X Muc C4 having prolines at both Position +1 and +3 suggests that the latter having a stronger GalNAc acceptor activity can be used more advantageously for the efficient glycosylation in producing glycoproteins having mucin type sugar chains in vivo.

What is claimed is:

1. A method for producing a modified protein or peptide having a mucin-type sugar chain, comprising culturing eukaryotic cells transformed with a chimeric DNA molecule encoding said modified protein or peptide, and collecting said modified protein or peptide produced by said eukaryotic cells, wherein said chimeric DNA molecule is prepared by providing a DNA molecule encoding a protein or peptide, and inserting into said DNA molecule a polynucleotide sequence encoding a peptide represented by formula (I):

$$X(-1)\text{-}X(0)\text{-}X(1)\text{-}X(2)\text{-}X(3) \tag{I}$$

wherein
X(-1) is selected from the group consisting of Y, A, W, S, G, V, F, T, and I,
X(0) is T or S,
X(2) is selected from the group consisting of A, P, C, K, R, H, S, M, T, Q, V, I, L and E, and X(l) and X(3) independently can be any amino acid, provided that at least one of X(1) and X(3) represents P.

2. The method according to claim 1, wherein X(0) is T.

3. The method according to claim 1, wherein said polynucleotide molecule further encodes one or two additional amino acids at the N-terminal side of X(-1), wherein said additional amino acids are selected from the group consisting of A, P, G, E, Q, T, R, and D.

4. The method according to claim 1, wherein the peptide represented by formula (I) is selected from the group consisting of:

ATPAP,
AATPAP,
AAATPAA,
AAATAAP,
PAATAAP,
APATAAP
AAPTAAP
AAATAPP
PAATPAP
APATPAP
AAXaTPXbP, where Xa and Xb can be any amino acid but either Xa or Xb is A, and
AAATPAPXc, where Xc can be any amino acid.

5. The method according to claim 1, wherein the eukaryotic cell is a mammalian cell.

6. The method according to claim 1, wherein said chimeric DNA molecule further comprises vector DNA.

7. A chimeric DNA molecule, comprising a polynucleotide sequence encoding a peptide represented by formula (I):

$$X(-1)\text{-}X(0)\text{-}X(1)\text{-}X(2)\text{-}X(3) \qquad (I)$$

wherein

X(-1) is selected from the group consisting of Y, A, W, S, G, V, F, T, and I,

X(0) is T or S,

X(2) is selected from the group consisting of A, P, C, K, R, H, S, M, T, Q, V, I, L and E, and X(1) and X(3) independently can be any amino acid, provided that at least one of X(1) and X(3) represents P.

8. A DNA molecule according to claim 7, wherein X(0) is T.

9. A DNA molecule according to claim 7, wherein said polynucleotide molecule further encodes one or two additional amino acids at the N-terminal side of X(-1), wherein said additional amino acids are selected from the group consisting of A, P, G, E, Q, T, R, and D.

10. The DNA molecule according to claim 7, wherein the peptide represented by formula (I) is selected from the group consisting of:

ATPAP,
AATPAP,
AAATPAA,
AAATAAP,
PAATAAP,
APATAAP
AAPTAAP
AAATAPP
PAATPAP
APATPAP
AAXaTPXbP, where Xa and Xb can be any amino acid but either Xa or Xb is A, and
AAATPAPXc, where Xc can be any amino acid.

11. A DNA molecule according to claim 7, further comprising vector DNA.

12. A eukaryotic host cell comprising a DNA molecule according to claim 11.

13. A eukaryotic host cell according to claims 12, wherein said cell is a mammalian cell.

* * * * *

SEQUENCE LISTING ( 1 ) GENERAL INFORMATION:

( i i i ) NUMBER OF SEQUENCES: 114

( 2 ) INFORMATION FOR SEQ ID NO:1:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: linear ( x i ) SEQUENCE DESCRIPTION: SEQ ID NO:1:

Pro  Gly  Gly  Ser  Ala  Thr  Pro  Gln
   1                   5

( 2 ) INFORMATION FOR SEQ ID NO:2:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: linear ( x i ) SEQUENCE DESCRIPTION: SEQ ID NO:2:

Ser  Gly  Gly  Ser  Gly  Thr  Pro  Gly
   1                   5

( 2 ) INFORMATION FOR SEQ ID NO:3:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: linear ( x i ) SEQUENCE DESCRIPTION: SEQ ID NO:3:

Gly  Glu  Pro  Thr  Ser  Thr  Pro
   1                   5

( 2 ) INFORMATION FOR SEQ ID NO:4:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: linear ( x i ) SEQUENCE DESCRIPTION: SEQ ID NO:4:

Pro  Asp  Ala  Ala  Ser  Ala  Ala  Pro
   1                   5

( 2 ) INFORMATION FOR SEQ ID NO:5:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: linear ( x i ) SEQUENCE DESCRIPTION: SEQ ID NO:5:

Ala  Leu  Gln  Pro  Thr  Gln  Gly  Ala
   1                   5

( 2 ) INFORMATION FOR SEQ ID NO:6:

( i ) SEQUENCE CHARACTERISTICS:
  ( A ) LENGTH: 5 amino acids
  ( B ) TYPE: amino acid
  ( C ) STRANDEDNESS: single
  ( D ) TOPOLOGY: linear ( x i ) SEQUENCE DESCRIPTION: SEQ ID NO:6:

Arg Thr Pro Pro Pro
1               5

( 2 ) INFORMATION FOR SEQ ID NO:7:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( x i ) SEQUENCE DESCRIPTION: SEQ ID NO:7:

Val Thr Arg Thr Pro Pro Pro
1               5

( 2 ) INFORMATION FOR SEQ ID NO:8:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( x i ) SEQUENCE DESCRIPTION: SEQ ID NO:8:

Pro Pro Ala Ser Thr Ser Ala Pro Gly
1               5

( 2 ) INFORMATION FOR SEQ ID NO:9:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( x i ) SEQUENCE DESCRIPTION: SEQ ID NO:9:

Arg Ser Pro Pro Pro
1               5

( 2 ) INFORMATION FOR SEQ ID NO:10:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( x i ) SEQUENCE DESCRIPTION: SEQ ID NO:10:

Arg Thr Pro Pro Pro
1               5

( 2 ) INFORMATION FOR SEQ ID NO:11:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( x i ) SEQUENCE DESCRIPTION: SEQ ID NO:11:

Pro Asp Ala Ala Ser Ala Ala Pro
1               5

( 2 ) INFORMATION FOR SEQ ID NO:12:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( x i ) SEQUENCE DESCRIPTION: SEQ ID NO:12:

```
Pro  Asp  Ala  Ala  Thr  Ala  Ala  Pro
1                        5
```

( 2 ) INFORMATION FOR SEQ ID NO:13:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:13:

```
Pro  Ala  Ala  Thr  Ala  Ala  Ala
1                   5
```

( 2 ) INFORMATION FOR SEQ ID NO:14:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:14:

```
Ala  Pro  Ala  Thr  Ala  Ala  Ala
1                   5
```

( 2 ) INFORMATION FOR SEQ ID NO:15:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:15:

```
Ala  Ala  Pro  Thr  Ala  Ala  Ala
1                   5
```

( 2 ) INFORMATION FOR SEQ ID NO:16:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:16:

```
Ala  Ala  Ala  Thr  Pro  Ala  Ala
1                   5
```

( 2 ) INFORMATION FOR SEQ ID NO:17:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:17:

Ala Ala Ala Thr Ala Pro Ala
1               5

( 2 ) INFORMATION FOR SEQ ID NO:18:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:18:

Ala Ala Ala Thr Ala Ala Pro
1               5

( 2 ) INFORMATION FOR SEQ ID NO:19:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:19:

Ala Ala Ala Thr Ala Ala Ala
1               5

( 2 ) INFORMATION FOR SEQ ID NO:20:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:20:

Pro Ala Ala Thr Ala Ala Pro
1               5

( 2 ) INFORMATION FOR SEQ ID NO:21:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:21:

Ala Pro Ala Thr Ala Ala Pro
1               5

( 2 ) INFORMATION FOR SEQ ID NO:22:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:22:

Ala Ala Pro Thr Ala Ala Pro
1               5

( 2 ) INFORMATION FOR SEQ ID NO:23:

( i ) SEQUENCE CHARACTERISTICS:
        ( A ) LENGTH: 7 amino acids (B) TYPE: amino acid
(C) STRANDEDNESS: single
(D) TOPOLOGY: linear (xi) SEQUENCE DESCRIPTION: SEQ ID NO:23:

Ala Ala Ala Thr Pro Ala Pro
1               5

(2) INFORMATION FOR SEQ ID NO:24:

(i) SEQUENCE CHARACTERISTICS:
(A) LENGTH: 7 amino acids
(B) TYPE: amino acid
(C) STRANDEDNESS: single
(D) TOPOLOGY: linear (xi) SEQUENCE DESCRIPTION: SEQ ID NO:24:

Ala Ala Ala Thr Ala Pro Pro
1               5

(2) INFORMATION FOR SEQ ID NO:25:

(i) SEQUENCE CHARACTERISTICS:
(A) LENGTH: 7 amino acids
(B) TYPE: amino acid
(C) STRANDEDNESS: single
(D) TOPOLOGY: linear (xi) SEQUENCE DESCRIPTION: SEQ ID NO:25:

Pro Ala Ala Thr Pro Ala Pro
1               5

(2) INFORMATION FOR SEQ ID NO:26:

(i) SEQUENCE CHARACTERISTICS:
(A) LENGTH: 7 amino acids
(B) TYPE: amino acid
(C) STRANDEDNESS: single
(D) TOPOLOGY: linear (xi) SEQUENCE DESCRIPTION: SEQ ID NO:26:

Ala Pro Ala Thr Pro Ala Pro
1               5

(2) INFORMATION FOR SEQ ID NO:27:

(i) SEQUENCE CHARACTERISTICS:
(A) LENGTH: 7 amino acids
(B) TYPE: amino acid
(C) STRANDEDNESS: single
(D) TOPOLOGY: linear (xi) SEQUENCE DESCRIPTION: SEQ ID NO:27:

Ala Ala Pro Thr Pro Ala Pro
1               5

(2) INFORMATION FOR SEQ ID NO:28:

(i) SEQUENCE CHARACTERISTICS:
(A) LENGTH: 7 amino acids
(B) TYPE: amino acid
(C) STRANDEDNESS: single
(D) TOPOLOGY: linear (xi) SEQUENCE DESCRIPTION: SEQ ID NO:28:

Ala Ala Ala Thr Pro Pro Pro
1               5

(2) INFORMATION FOR SEQ ID NO:29:

(i) SEQUENCE CHARACTERISTICS:
        (A) LENGTH: 13 amino acids
        (B) TYPE: amino acid
        (C) STRANDEDNESS: single
        (D) TOPOLOGY: linear (xi) SEQUENCE DESCRIPTION: SEQ ID NO:29:

Gly Gly Lys Ala Pro Thr Ser Ser Ser Thr Lys Gly Gly
1               5                   10

(2) INFORMATION FOR SEQ ID NO:30:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:30:

Thr Pro Ala Pro
1

(2) INFORMATION FOR SEQ ID NO:31:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:31:

Ala Thr Pro Ala Pro
1               5

(2) INFORMATION FOR SEQ ID NO:32:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:32:

Ala Ala Thr Pro Ala Pro
1               5

(2) INFORMATION FOR SEQ ID NO:33:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:33:

Ala Ala Ala Thr Pro Cys Pro
1               5

(2) INFORMATION FOR SEQ ID NO:34:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:34:

```
   Ala   Ala   Ala   Thr   Pro   Lys   Pro
   1                       5
```

( 2 ) INFORMATION FOR SEQ ID NO:35:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:35:

```
   Ala   Ala   Ala   Thr   Pro   Arg   Pro
   1                       5
```

( 2 ) INFORMATION FOR SEQ ID NO:36:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:36:

```
   Ala   Ala   Ala   Thr   Pro   His   Pro
   1                       5
```

( 2 ) INFORMATION FOR SEQ ID NO:37:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:37:

```
   Ala   Ala   Ala   Thr   Pro   Ser   Pro
   1                       5
```

( 2 ) INFORMATION FOR SEQ ID NO:38:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:38:

```
   Ala   Ala   Ala   Thr   Pro   Met   Pro
   1                       5
```

( 2 ) INFORMATION FOR SEQ ID NO:39:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:39:

```
   Ala   Ala   Ala   Thr   Pro   Thr   Pro
   1                       5
```

( 2 ) INFORMATION FOR SEQ ID NO:40:

( i ) SEQUENCE CHARACTERISTICS:
        ( A ) LENGTH: 7 amino acids
        ( B ) TYPE: amino acid
        ( C ) STRANDEDNESS: single (D) TOPOLOGY: linear (xi) SEQUENCE DESCRIPTION: SEQ ID NO:40:

Ala Ala Ala Thr Pro Gln Pro
1               5

(2) INFORMATION FOR SEQ ID NO:41:

(i) SEQUENCE CHARACTERISTICS:
　　　　(A) LENGTH: 7 amino acids
　　　　(B) TYPE: amino acid
　　　　(C) STRANDEDNESS: single
　　　　(D) TOPOLOGY: linear (xi) SEQUENCE DESCRIPTION: SEQ ID NO:41:

Ala Ala Ala Thr Pro Val Pro
1               5

(2) INFORMATION FOR SEQ ID NO:42:

(i) SEQUENCE CHARACTERISTICS:
　　　　(A) LENGTH: 7 amino acids
　　　　(B) TYPE: amino acid
　　　　(C) STRANDEDNESS: single
　　　　(D) TOPOLOGY: linear (xi) SEQUENCE DESCRIPTION: SEQ ID NO:42:

Ala Ala Ala Thr Pro Ile Pro
1               5

(2) INFORMATION FOR SEQ ID NO:43:

(i) SEQUENCE CHARACTERISTICS:
　　　　(A) LENGTH: 7 amino acids
　　　　(B) TYPE: amino acid
　　　　(C) STRANDEDNESS: single
　　　　(D) TOPOLOGY: linear (xi) SEQUENCE DESCRIPTION: SEQ ID NO:43:

Ala Ala Ala Thr Pro Leu Pro
1               5

(2) INFORMATION FOR SEQ ID NO:44:

(i) SEQUENCE CHARACTERISTICS:
　　　　(A) LENGTH: 7 amino acids
　　　　(B) TYPE: amino acid
　　　　(C) STRANDEDNESS: single
　　　　(D) TOPOLOGY: linear (xi) SEQUENCE DESCRIPTION: SEQ ID NO:44:

Ala Ala Ala Thr Pro Glu Pro
1               5

(2) INFORMATION FOR SEQ ID NO:45:

(i) SEQUENCE CHARACTERISTICS:
　　　　(A) LENGTH: 7 amino acids
　　　　(B) TYPE: amino acid
　　　　(C) STRANDEDNESS: single
　　　　(D) TOPOLOGY: linear (xi) SEQUENCE DESCRIPTION: SEQ ID NO:45:

Ala Ala Ala Thr Pro Gly Pro
1               5

(2) INFORMATION FOR SEQ ID NO:46:

(i) SEQUENCE CHARACTERISTICS:
  (A) LENGTH: 7 amino acids
  (B) TYPE: amino acid
  (C) STRANDEDNESS: single
  (D) TOPOLOGY: linear (xi) SEQUENCE DESCRIPTION: SEQ ID NO:46:

Ala Ala Ala Thr Pro Tyr Pro
1               5

(2) INFORMATION FOR SEQ ID NO:47:

(i) SEQUENCE CHARACTERISTICS:
    (A) LENGTH: 7 amino acids
    (B) TYPE: amino acid
    (C) STRANDEDNESS: single
    (D) TOPOLOGY: linear (xi) SEQUENCE DESCRIPTION: SEQ ID NO:47:

Ala Ala Ala Thr Pro Trp Pro
1               5

(2) INFORMATION FOR SEQ ID NO:48:

(i) SEQUENCE CHARACTERISTICS:
    (A) LENGTH: 7 amino acids
    (B) TYPE: amino acid
    (C) STRANDEDNESS: single
    (D) TOPOLOGY: linear (xi) SEQUENCE DESCRIPTION: SEQ ID NO:48:

Ala Ala Ala Thr Pro Phe Pro
1               5

(2) INFORMATION FOR SEQ ID NO:49:

(i) SEQUENCE CHARACTERISTICS:
    (A) LENGTH: 7 amino acids
    (B) TYPE: amino acid
    (C) STRANDEDNESS: single
    (D) TOPOLOGY: linear (xi) SEQUENCE DESCRIPTION: SEQ ID NO:49:

Ala Ala Ala Thr Pro Asn Pro
1               5

(2) INFORMATION FOR SEQ ID NO:50:

(i) SEQUENCE CHARACTERISTICS:
    (A) LENGTH: 7 amino acids
    (B) TYPE: amino acid
    (C) STRANDEDNESS: single
    (D) TOPOLOGY: linear (xi) SEQUENCE DESCRIPTION: SEQ ID NO:50:

Ala Ala Ala Thr Pro Asp Pro
1               5

(2) INFORMATION FOR SEQ ID NO:51:

(i) SEQUENCE CHARACTERISTICS:
    (A) LENGTH: 7 amino acids
    (B) TYPE: amino acid
    (C) STRANDEDNESS: single
    (D) TOPOLOGY: linear (xi) SEQUENCE DESCRIPTION: SEQ ID NO:51:

Ala Ala Tyr Thr Pro Ala Pro
1               5

( 2 ) INFORMATION FOR SEQ ID NO:52:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:52:

```
Ala  Ala  Trp  Thr  Pro  Ala  Pro
 1                   5
```

( 2 ) INFORMATION FOR SEQ ID NO:53:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:53:

```
Ala  Ala  Ser  Thr  Pro  Ala  Pro
 1                   5
```

( 2 ) INFORMATION FOR SEQ ID NO:54:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:54:

```
Ala  Ala  Gly  Thr  Pro  Ala  Pro
 1                   5
```

( 2 ) INFORMATION FOR SEQ ID NO:55:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:55:

```
Ala  Ala  Val  Thr  Pro  Ala  Pro
 1                   5
```

( 2 ) INFORMATION FOR SEQ ID NO:56:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:56:

```
Ala  Ala  Phe  Thr  Pro  Ala  Pro
 1                   5
```

( 2 ) INFORMATION FOR SEQ ID NO:57:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:57:

Ala Ala Thr Thr Pro Ala Pro
1               5

( 2 ) INFORMATION FOR SEQ ID NO:58:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( x i ) SEQUENCE DESCRIPTION: SEQ ID NO:58:

Ala Ala Ile Thr Pro Ala Pro
1               5

( 2 ) INFORMATION FOR SEQ ID NO:59:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( x i ) SEQUENCE DESCRIPTION: SEQ ID NO:59:

Ala Ala His Thr Pro Ala Pro
1               5

( 2 ) INFORMATION FOR SEQ ID NO:60:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( x i ) SEQUENCE DESCRIPTION: SEQ ID NO:60:

Ala Ala Met Thr Pro Ala Pro
1               5

( 2 ) INFORMATION FOR SEQ ID NO:61:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( x i ) SEQUENCE DESCRIPTION: SEQ ID NO:61:

Ala Ala Gln Thr Pro Ala Pro
1               5

( 2 ) INFORMATION FOR SEQ ID NO:62:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( x i ) SEQUENCE DESCRIPTION: SEQ ID NO:62:

Ala Ala Cys Thr Pro Ala Pro
1               5

( 2 ) INFORMATION FOR SEQ ID NO:63:

( i ) SEQUENCE CHARACTERISTICS:
    ( A ) LENGTH: 7 amino acids (B) TYPE: amino acid
(C) STRANDEDNESS: single
(D) TOPOLOGY: linear (xi) SEQUENCE DESCRIPTION: SEQ ID NO:63:

Ala Ala Asn Thr Pro Ala Pro
1               5

(2) INFORMATION FOR SEQ ID NO:64:

(i) SEQUENCE CHARACTERISTICS:
(A) LENGTH: 7 amino acids
(B) TYPE: amino acid
(C) STRANDEDNESS: single
(D) TOPOLOGY: linear (xi) SEQUENCE DESCRIPTION: SEQ ID NO:64:

Ala Ala Leu Thr Pro Ala Pro
1               5

(2) INFORMATION FOR SEQ ID NO:65:

(i) SEQUENCE CHARACTERISTICS:
(A) LENGTH: 7 amino acids
(B) TYPE: amino acid
(C) STRANDEDNESS: single
(D) TOPOLOGY: linear (xi) SEQUENCE DESCRIPTION: SEQ ID NO:65:

Ala Ala Arg Thr Pro Ala Pro
1               5

(2) INFORMATION FOR SEQ ID NO:66:

(i) SEQUENCE CHARACTERISTICS:
(A) LENGTH: 7 amino acids
(B) TYPE: amino acid
(C) STRANDEDNESS: single
(D) TOPOLOGY: linear (xi) SEQUENCE DESCRIPTION: SEQ ID NO:66:

Ala Ala Glu Thr Pro Ala Pro
1               5

(2) INFORMATION FOR SEQ ID NO:67:

(i) SEQUENCE CHARACTERISTICS:
(A) LENGTH: 7 amino acids
(B) TYPE: amino acid
(C) STRANDEDNESS: single
(D) TOPOLOGY: linear (xi) SEQUENCE DESCRIPTION: SEQ ID NO:67:

Ala Ala Asp Thr Pro Ala Pro
1               5

(2) INFORMATION FOR SEQ ID NO:68:

(i) SEQUENCE CHARACTERISTICS:
(A) LENGTH: 7 amino acids
(B) TYPE: amino acid
(C) STRANDEDNESS: single
(D) TOPOLOGY: linear (xi) SEQUENCE DESCRIPTION: SEQ ID NO:68:

Ala Ala Lys Thr Pro Ala Pro
1               5

( 2 ) INFORMATION FOR SEQ ID NO:69:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( x i ) SEQUENCE DESCRIPTION: SEQ ID NO:69:

```
Ala  Ala  Ala  Thr  Pro  Ala  Pro  Gly
1                  5
```

( 2 ) INFORMATION FOR SEQ ID NO:70:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( x i ) SEQUENCE DESCRIPTION: SEQ ID NO:70:

```
Ala  Ala  Ala  Thr  Pro  Ala  Pro  Gln
1                  5
```

( 2 ) INFORMATION FOR SEQ ID NO:71:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( x i ) SEQUENCE DESCRIPTION: SEQ ID NO:71:

```
Ala  Ala  Ala  Thr  Pro  Ala  Pro  Glu
1                  5
```

( 2 ) INFORMATION FOR SEQ ID NO:72:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( x i ) SEQUENCE DESCRIPTION: SEQ ID NO:72:

```
Ala  Ala  Ala  Thr  Pro  Ala  Pro  Ala
1                  5
```

( 2 ) INFORMATION FOR SEQ ID NO:73:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( x i ) SEQUENCE DESCRIPTION: SEQ ID NO:73:

```
Ala  Ala  Ala  Thr  Pro  Ala  Pro  Asn
1                  5
```

( 2 ) INFORMATION FOR SEQ ID NO:74:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( x i ) SEQUENCE DESCRIPTION: SEQ ID NO:74:

Ala Ala Ala Thr Pro Ala Pro Asp
1               5

( 2 ) INFORMATION FOR SEQ ID NO:75:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( x i ) SEQUENCE DESCRIPTION: SEQ ID NO:75:

Ala Ala Ala Thr Pro Ala Pro Arg
1               5

( 2 ) INFORMATION FOR SEQ ID NO:76:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( x i ) SEQUENCE DESCRIPTION: SEQ ID NO:76:

Ala Ala Ala Thr Pro Ala Pro Cys
1               5

( 2 ) INFORMATION FOR SEQ ID NO:77:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( x i ) SEQUENCE DESCRIPTION: SEQ ID NO:77:

Ala Ala Ala Thr Pro Ala Pro Ile
1               5

( 2 ) INFORMATION FOR SEQ ID NO:78:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( x i ) SEQUENCE DESCRIPTION: SEQ ID NO:78:

Ala Ala Ala Thr Pro Ala Pro Val
1               5

( 2 ) INFORMATION FOR SEQ ID NO:79:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( x i ) SEQUENCE DESCRIPTION: SEQ ID NO:79:

Ala Ala Ala Thr Pro Ala Pro Ser
1               5

( 2 ) INFORMATION FOR SEQ ID NO:80:

( i ) SEQUENCE CHARACTERISTICS:
    ( A ) LENGTH: 8 amino acids
    ( B ) TYPE: amino acid
    ( C ) STRANDEDNESS: single ( D ) TOPOLOGY: linear ( x i ) SEQUENCE DESCRIPTION: SEQ ID NO:80:

Ala Ala Ala Thr Pro Ala Pro Lys
1               5

( 2 ) INFORMATION FOR SEQ ID NO:81:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: linear ( x i ) SEQUENCE DESCRIPTION: SEQ ID NO:81:

Ala Ala Ala Thr Pro Ala Pro Tyr
1               5

( 2 ) INFORMATION FOR SEQ ID NO:82:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: linear ( x i ) SEQUENCE DESCRIPTION: SEQ ID NO:82:

Ala Ala Ala Thr Pro Ala Pro Leu
1               5

( 2 ) INFORMATION FOR SEQ ID NO:83:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: linear ( x i ) SEQUENCE DESCRIPTION: SEQ ID NO:83:

Ala Ala Ala Thr Pro Ala Pro Thr
1               5

( 2 ) INFORMATION FOR SEQ ID NO:84:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: linear ( x i ) SEQUENCE DESCRIPTION: SEQ ID NO:84:

Ala Ala Ala Thr Pro Ala Pro Trp
1               5

( 2 ) INFORMATION FOR SEQ ID NO:85:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: linear ( x i ) SEQUENCE DESCRIPTION: SEQ ID NO:85:

Ala Ala Ala Thr Pro Ala Pro Met
1               5

( 2 ) INFORMATION FOR SEQ ID NO:86:

( i ) SEQUENCE CHARACTERISTICS:
  ( A ) LENGTH: 8 amino acids
  ( B ) TYPE: amino acid
  ( C ) STRANDEDNESS: single
  ( D ) TOPOLOGY: linear ( x i ) SEQUENCE DESCRIPTION: SEQ ID NO:86:

Ala Ala Ala Thr Pro Ala Pro Pro
1               5

( 2 ) INFORMATION FOR SEQ ID NO:87:

( i ) SEQUENCE CHARACTERISTICS:
  ( A ) LENGTH: 8 amino acids
  ( B ) TYPE: amino acid
  ( C ) STRANDEDNESS: single
  ( D ) TOPOLOGY: linear ( x i ) SEQUENCE DESCRIPTION: SEQ ID NO:87:

Ala Ala Ala Thr Pro Ala Pro Phe
1               5

( 2 ) INFORMATION FOR SEQ ID NO:88:

( i ) SEQUENCE CHARACTERISTICS:
  ( A ) LENGTH: 8 amino acids
  ( B ) TYPE: amino acid
  ( C ) STRANDEDNESS: single
  ( D ) TOPOLOGY: linear ( x i ) SEQUENCE DESCRIPTION: SEQ ID NO:88:

Ala Ala Ala Thr Pro Ala Pro His
1               5

( 2 ) INFORMATION FOR SEQ ID NO:89:

( i ) SEQUENCE CHARACTERISTICS:
  ( A ) LENGTH: 47 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:89:

AAGGATCCCC ATGGCAGCAG CAACGCCGGC ACCCATGGGG AATTCAA         4 7

( 2 ) INFORMATION FOR SEQ ID NO:90:

( i ) SEQUENCE CHARACTERISTICS:
  ( A ) LENGTH: 47 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:90:

TTGAATTCCC CATGGGTGCC GGCGTTGCTG CTGCCATGGG GATCCTT         4 7

( 2 ) INFORMATION FOR SEQ ID NO:91:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:91:

GTATCCATGG CCCCTATACT AGGTTATTGG         3 0

( 2 ) INFORMATION FOR SEQ ID NO:92:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:92:

TACTGCAGTC AGTCAGTCAC GATGAATTCC     30

( 2 ) INFORMATION FOR SEQ ID NO:93:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:93:

ATGGTACCAT GCGCGCCATT ACCGAGT     27

( 2 ) INFORMATION FOR SEQ ID NO:94:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:94:

CCGAGCTCTG TTTCCTGTGT GAAATTGT     28

( 2 ) INFORMATION FOR SEQ ID NO:95:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:95:

CAGAGCTCAT GTCCCCTATA CTAGGTTA     28

( 2 ) INFORMATION FOR SEQ ID NO:96:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:96:

GGACTAGTCA TGTTGTGCTT GTCAGCTA     28

( 2 ) INFORMATION FOR SEQ ID NO:97:

( i ) SEQUENCE CHARACTERISTICS:
    ( A ) LENGTH: 45 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:97:

CGTCTAGACC GTCAGTCAGT CACGATGAAG GCGCGGGGGT CCCAC     45

( 2 ) INFORMATION FOR SEQ ID NO:98:

( i ) SEQUENCE CHARACTERISTICS:

(A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:98:

CGTCTAGACC GTCAGTCAGT CACTATTAAG GCGCGGGGGT CCCAC        45

(2) INFORMATION FOR SEQ ID NO:99:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:99:

CGTCTAGACC GTCAGTCAGT CACGATGAAG GCCCGGGGGT CCCAC        45

(2) INFORMATION FOR SEQ ID NO:100:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:100:

AACTCGAGAA TTCATGGGGG TGCACGAATG        30

(2) INFORMATION FOR SEQ ID NO:101:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:101:

CAATAACCTA GTATAGGGGA GCCCAGGACT GGGAGGCCCA        40

(2) INFORMATION FOR SEQ ID NO:102:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:102:

TGGGCCTCCC AGTCCTGGGC TCCCCTATAC TAGGTTATTG        40

(2) INFORMATION FOR SEQ ID NO:103:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:103:

CCTCTAGATC GTCAGTCAGT CACGATGAAT        30

(2) INFORMATION FOR SEQ ID NO:104:

(i) SEQUENCE CHARACTERISTICS:
        (A) LENGTH: 8 amino acids
        (B) TYPE: amino acid ( C ) STRANDEDNESS: single
( D ) TOPOLOGY: linear ( x i ) SEQUENCE DESCRIPTION: SEQ ID NO:104:

Met Ala Ala Ala Thr Pro Ala Pro
1               5

( 2 ) INFORMATION FOR SEQ ID NO:105:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( x i ) SEQUENCE DESCRIPTION: SEQ ID NO:105:

Met Ala Ala Ala Thr Pro Ala Pro Met
1               5

( 2 ) INFORMATION FOR SEQ ID NO:106:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( x i ) SEQUENCE DESCRIPTION: SEQ ID NO:106:

GTTGACAATT AATCATCCGG CTCGT 25

( 2 ) INFORMATION FOR SEQ ID NO:107:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( x i ) SEQUENCE DESCRIPTION: SEQ ID NO:107:

CGTCTAGACC GTCAGTCAGT CACGATGAAT TGCCGGGGGT CCCAC 45

( 2 ) INFORMATION FOR SEQ ID NO:108:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( x i ) SEQUENCE DESCRIPTION: SEQ ID NO:108:

Pro Arg Thr Pro Pro Pro
1               5

( 2 ) INFORMATION FOR SEQ ID NO:109:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( x i ) SEQUENCE DESCRIPTION: SEQ ID NO:109:

Thr Pro Arg Thr Pro Pro Pro
1               5

( 2 ) INFORMATION FOR SEQ ID NO:110:

( i ) SEQUENCE CHARACTERISTICS:

-continued (A) LENGTH: 9 amino acids
(B) TYPE: amino acid
(C) STRANDEDNESS: single
(D) TOPOLOGY: linear (xi) SEQUENCE DESCRIPTION: SEQ ID NO:110:

Pro Asp Thr Arg Pro Ala Pro Gly Ser
1               5

(2) INFORMATION FOR SEQ ID NO:111:

(i) SEQUENCE CHARACTERISTICS:
(A) LENGTH: 9 amino acids
(B) TYPE: amino acid
(C) STRANDEDNESS: single
(D) TOPOLOGY: linear (xi) SEQUENCE DESCRIPTION: SEQ ID NO:111:

Pro Asp Thr Arg Pro Pro Ala Gly Ser
1               5

(2) INFORMATION FOR SEQ ID NO:112:

(i) SEQUENCE CHARACTERISTICS:
(A) LENGTH: 9 amino acids
(B) TYPE: amino acid
(C) STRANDEDNESS: single
(D) TOPOLOGY: linear (xi) SEQUENCE DESCRIPTION: SEQ ID NO:112:

Pro Asp Thr Arg Ala Pro Pro Gly Ser
1               5

(2) INFORMATION FOR SEQ ID NO:113:

(i) SEQUENCE CHARACTERISTICS:
(A) LENGTH: 12 amino acids
(B) TYPE: amino acid
(C) STRANDEDNESS: single
(D) TOPOLOGY: linear (xi) SEQUENCE DESCRIPTION: SEQ ID NO:113:

Gly Gly Lys Ala Pro Thr Pro Pro Pro Lys Gly Gly
1               5                   10

(2) INFORMATION FOR SEQ ID NO:114:

(i) SEQUENCE CHARACTERISTICS:
(A) LENGTH: 12 amino acids
(B) TYPE: amino acid
(C) STRANDEDNESS: single
(D) TOPOLOGY: linear (xi) SEQUENCE DESCRIPTION: SEQ ID NO:114:

Pro His Met Ala Gln Val Thr Val Gly Pro Gly Leu
1               5                   10